(12) United States Patent  
Berry et al.

(10) Patent No.: US 9,333,240 B2  
(45) Date of Patent: May 10, 2016

(54) COMPOUNDS FOR IMPROVING NUTRITIONAL STATUS, COGNITION AND SURVIVAL

(75) Inventors: Elliot Berry, Jerusalem (IL); Yosefa Avraham, Jerusalem (IL); Yossi Dagon, Nes-Ziona (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 919 days.

(21) Appl. No.: 11/991,750

(22) PCT Filed: Sep. 14, 2006

(86) PCT No.: PCT/IL2006/001087  
§ 371 (c)(1),  
(2), (4) Date: Feb. 20, 2009

(87) PCT Pub. No.: WO2007/032013  
PCT Pub. Date: Apr. 19, 2007

(65) Prior Publication Data  
US 2009/0175841 A1 Jul. 9, 2009

Related U.S. Application Data

(60) Provisional application No. 60/717,247, filed on Sep. 16, 2005.

(51) Int. Cl.  
*A61K 38/45* (2006.01)  
*A61K 38/22* (2006.01)  
*A61K 31/155* (2006.01)

(52) U.S. Cl.  
CPC .............. *A61K 38/22* (2013.01); *A61K 31/155* (2013.01); *A61K 38/2264* (2013.01); *A61K 38/45* (2013.01)

(58) Field of Classification Search  
CPC .................................................. A61K 2300/00  
USPC ............................................... 424/9.2, 9.411  
See application file for complete search history.

(56) References Cited

U.S. PATENT DOCUMENTS 6,630,444 B1 10/2003 Schwartz et al.

FOREIGN PATENT DOCUMENTS

WO 99/46283 9/1999

OTHER PUBLICATIONS

Takahashi et al. "Leptin induces mitogen-activated protein kinase-dependent proliferation of C3H10T1/2 cells", JBC, 1997, 272(20):12897-12900.*
Chehab et al. "Correction of the sterility defect in homozygous obese female mice by treatment with the human recombinant leptin", Nature Genetics, 1996, 12:318-320.*
Faggioni et al. "Reduced leptin levels in starvation increase susceptibility to endotoxic shock", American J of Pathology, 2000, 156(5):1781-1787.*
Fewlass et al. "Obesity-related leptin regulates Alzheimer's Abeta", The FASEB J, 2004, 18:1870-1878.*
Zhang et al., "Positional Cloning of the Mouse Obese Gene and its Human Homologue," Nature, vol. 372, Dec. 1994, pp. 425-432.
Tunek, et al., "Hydrolysis of 3H-Bambuterol, a Carbamate Prodrug of Terbutaline, in Blood From Humans and Laboratory Animals in Vitro," Biochemical Pharmacology, vol. 37, No. 20, 1988, pp. 3867-3876.
King et al., "Interaction of Carboxypeptidase A with Carbamate and Carbonate Esters," Biochemistry, vol. 26, 1987, pp. 2294-2300.
Lindberg, et al., "Metabolism of Bambuterol in Rat Liver Microsomes: Identification of Hydroxylated an Demethylated Products by Liquid Chromatography Mass Spectometry," Drug Metabolism and Disposition, vol. 17, No. 3, 1989, pp. 311-322.
Anderson, et al., "Glutathione Monoethyl Ester Provides Neuroprotection in a Rat Model of Stroke," Neuroscience Letters 354, 2004, pp. 163-165.
Singhal, et al., "Glutathione, a First Line of Defense Against Cadmium Toxicity," FASEB J., 1987, pp. 220-223.
Morrison, et al., "Combinatorial Alanine-Scanning," Chemical Biology, vol. 5, 2001, pp. 302-307.
Zabrocki, et al., "Conformational Mimicry, 1. 1,5-Disubstituted Tetrazole Ring as a Surrogate for the Cis Amide Bond," Journal of American Chemical Society, vol. 110, 1998, pp. 5875-5880.
Jones et al., "Amide Bond Isosteres: Imidazolines in Pseudopeptide Chemistry," Tetrahedron Letters, vol. 29, No. 31, 1988, pp. 3853-3856.
Kemp at al., "Conformationally Restricted Cyclic Nonapeptides Derived from L-Cysteine and LL-3-Amino-2-Piperidone-6-Carboxylic Acid (LL-Acp), a Potent S-Turn-Inducing Dipeptide Analogue," Journal of Org. Chemistry, vol. 50, 1985, pp. 5834-5838.
Kemp et al., "Conformational Analysis of Peptide-Functionalized Diacylaminoepindolidiones 1H NHR Evidence for S-Sheet Formation," Tetrahedron Letters, vol. 29, No. 40, pp. 5081-5082.
Kemp at al., "A Convenient Preparation of Derivatives of 3(S)-Amino-10 (R)-Carboxy-1,6-Diaza-Cyclodeca-2, 7-Dione the Dilactam of L-A-Y-Diaminobutyric Acid and D-Glutamic Acid: A S-Turn Template," Tetrahedron Letters, vol. 29, No. 40, 1988, pp. 5057-5060.
Kemp et al., "(2S, 5S, 8S, 11S)-1-Acetyl-1, 4-Diaza-3-Keto-5-Carboxy-10-Thia-Tricyclo-[2.8.0 4,8]-Tridecane, 1 the Preferred Conformation of 1 (1=A Temp-OH) and its Peptide Conjugates—A Temp-L-)Ala)N-OR (n=1 to 4) and A-Temp-L-Ala-L-Phe-L-Lys(EBoc)-L-Lys-(EBoc)-NHMe—Studies of Templates for A-Helix Formation," Tetrahedron Letters, vol. 29, No. 39, 1988, pp. 4935-4938.

(Continued)

*Primary Examiner* — Bin Shen  
(74) *Attorney, Agent, or Firm* — Browdy and Neimark, PLLC

(57) ABSTRACT

The present invention concerns using a leptin protein, a variant fragment or mimic of a leptin protein, or an activator of the AMPK signal transduction pathway for preparing a medicament that can either be used to improve cognitive function or to treat treatment of undesirable manifestations of a nutritional stress condition and to prolong survival.

8 Claims, 14 Drawing Sheets

(56) References Cited

OTHER PUBLICATIONS

Kemp et al,. "Amino Acid Derivatives that Stabilize Secondary Structures of Polypetides. 4. Practical Synthesis of 4-(Alkylamino)-3-Cyano-6-Azabicyclo[3.2.1]oct-3-enes (Ben Derivatives) as Y-Turn Templates," Journal of Org. Chemistry, 1989, vol. 54, pp. 109-115.

Kahn et al., "The Incorporation of S-Turn Prosthetic Units into Merrifield Solid Phase Peptide Synthesis," Tetrahedron Letters, vol. 30, No. 18, 1989, pp. 2317-2320.

Nagai et al., "Synthesis of a Bicyclic Dipeptide with the Shape of S-Turn Central Part," Tetrahedron Letters, Vol, 26, No. 5, 1985, pp. 647-650.

Olson et al., "Design and Synthesis of a Protein S-Turn Mimetic," Journal of Am. Chem. Society, vol. 112, 1990, pp. 323-333.

Kazmierski et al., "Topographic Design of Peptide Neurotransmitters and Hormones on Stable Backbone Templates: Relation of Conformation and Dynamics to Bioactivity," Journal of Am. Chem. Society, vol. 113, 1991, pp. 2275-2283.

Kazmierski et al., "Asymmetric Synthesis of Topographically Constrained Amino Acids: Synthesis of the Optically Pure Isomers of A,S-Dimethyl-Phenylalanine and A,S-Dimethyl-1,2,3,4,-Tetrahydroisoquinoline-3-Carboxylic Acid," Tetrahedron Letters, vol. 32, No. 41, 1991, pp. 5769-5772.

International Search Report for International Application No. PCT/IL2006/001087 mailed Apr. 4, 2007.

Written Opinion of the International Searching Authority mailed Apr. 4, 2007.

H. J. Aizenstein et al.; Frequent Amyloid Deposition Without Significant Cognitive Impairment Among the Elderly, Arch Neuro/vol. 65 (No. 11), Nov. 2008; http://archneur.jamanetwork.com; pp. 1509-1517.

* cited by examiner

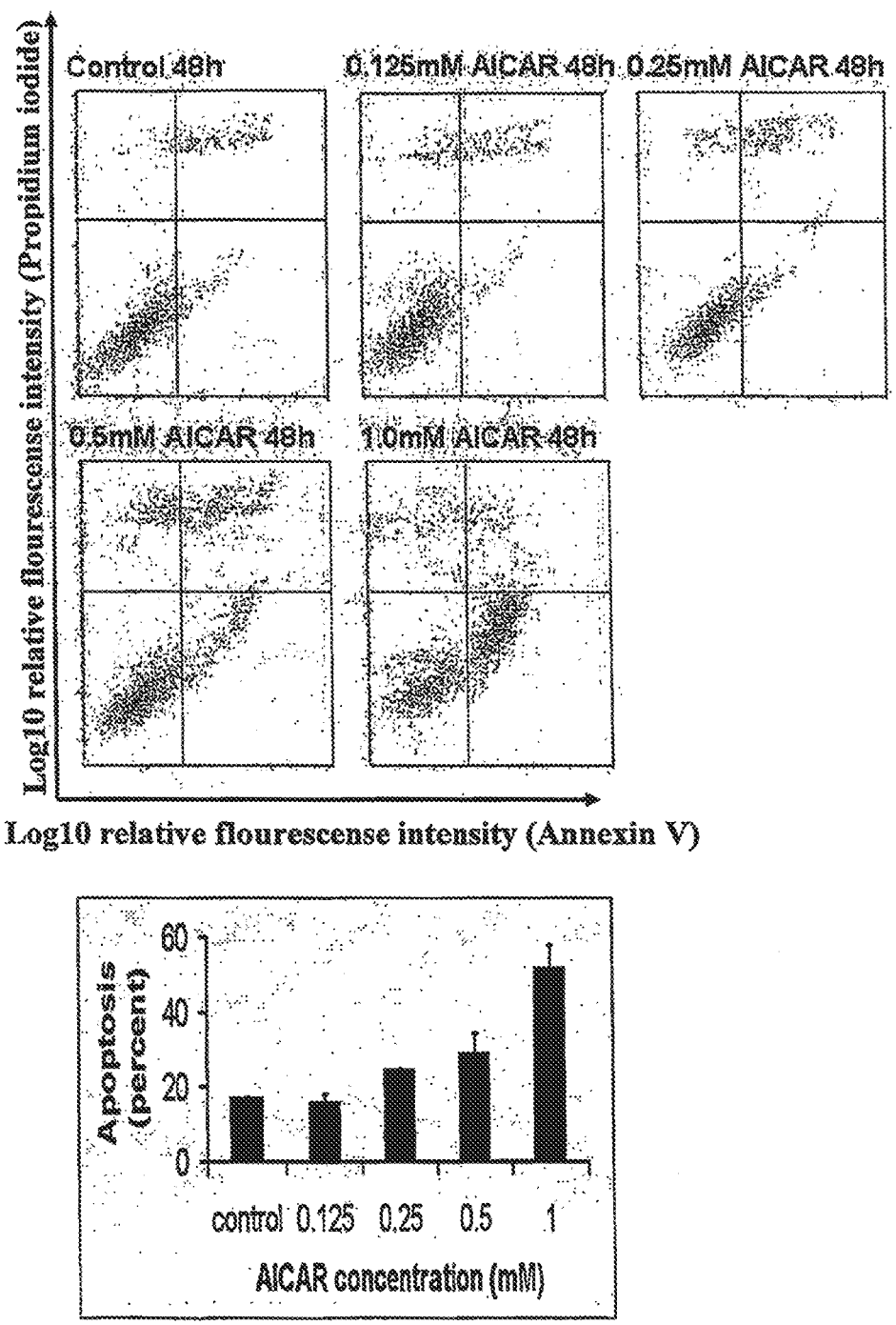

Fig. 3A
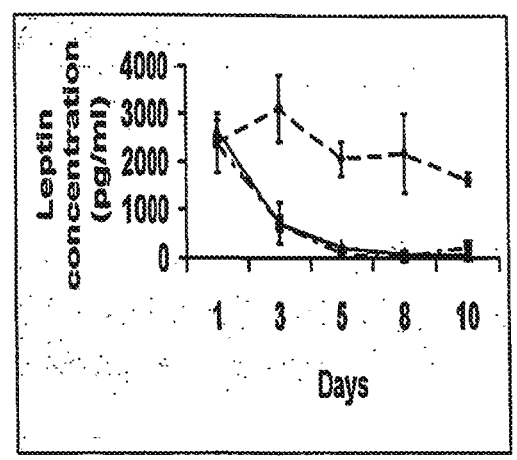
Fig. 3B
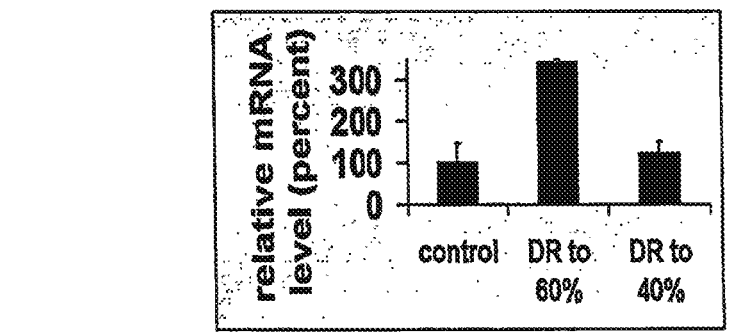
OBR-long →
β-actin →
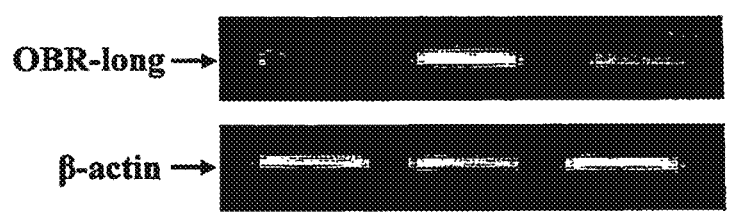
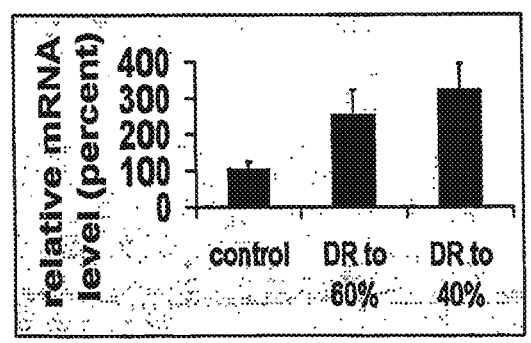
OBR-short →

Fig. 3C
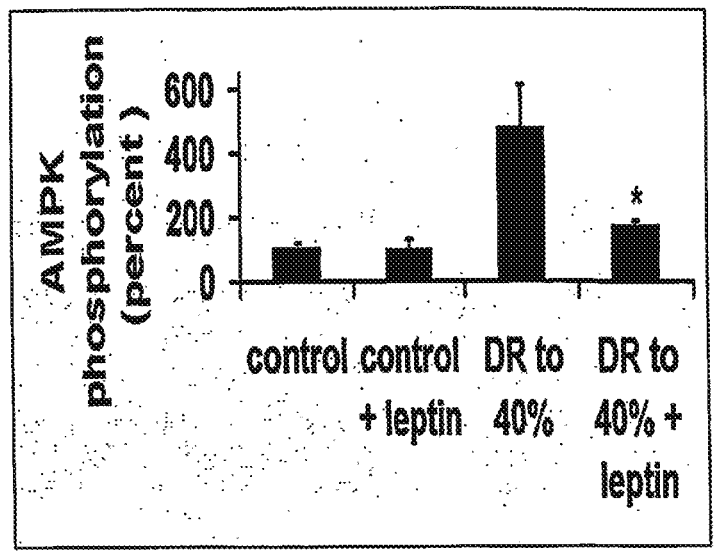
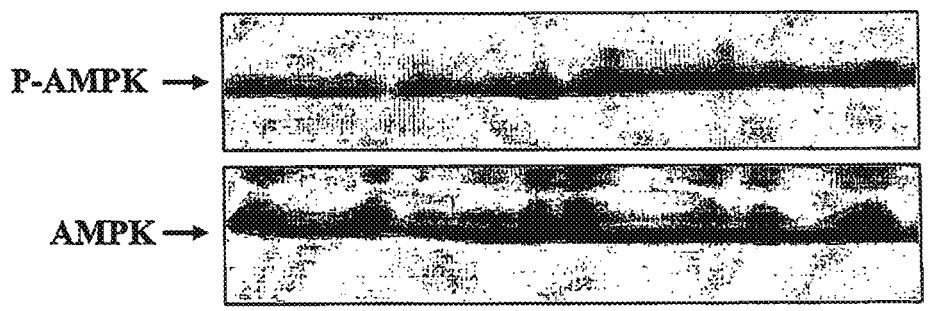
Fig. 4A
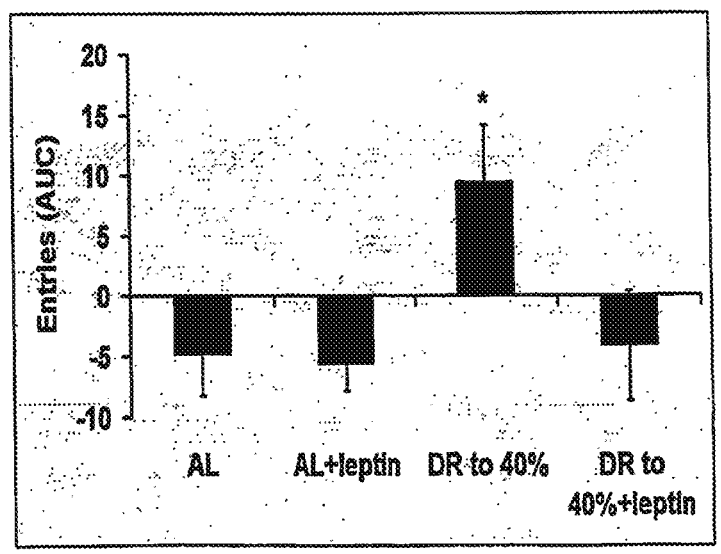

control    DR to 40%    DR to +40% leptin

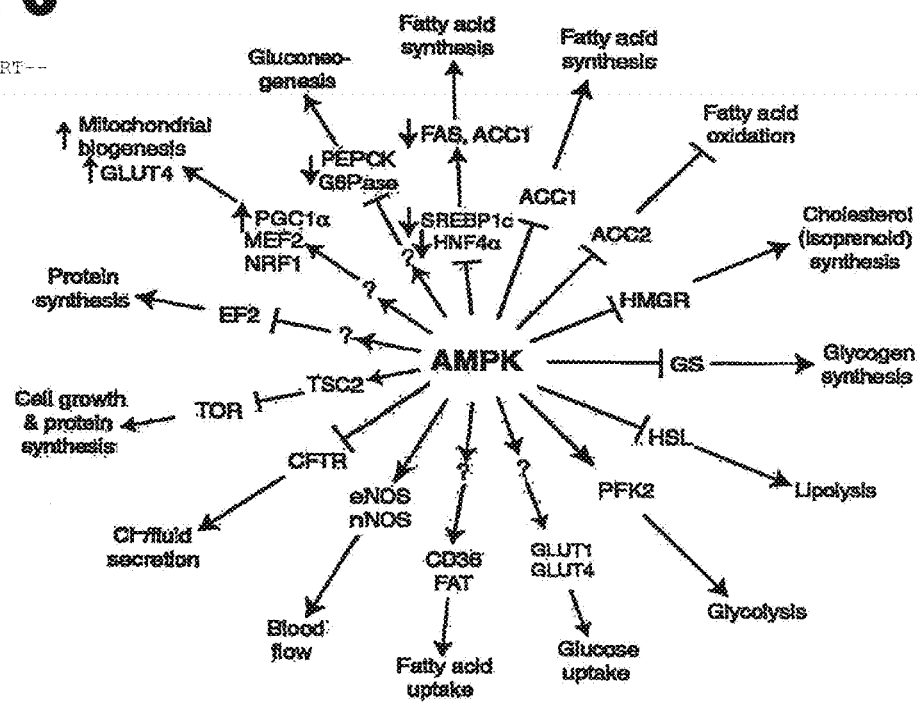
AMPK TARGETS
(Hardie, J of Cell Science 117, 5479-5487, 2004)
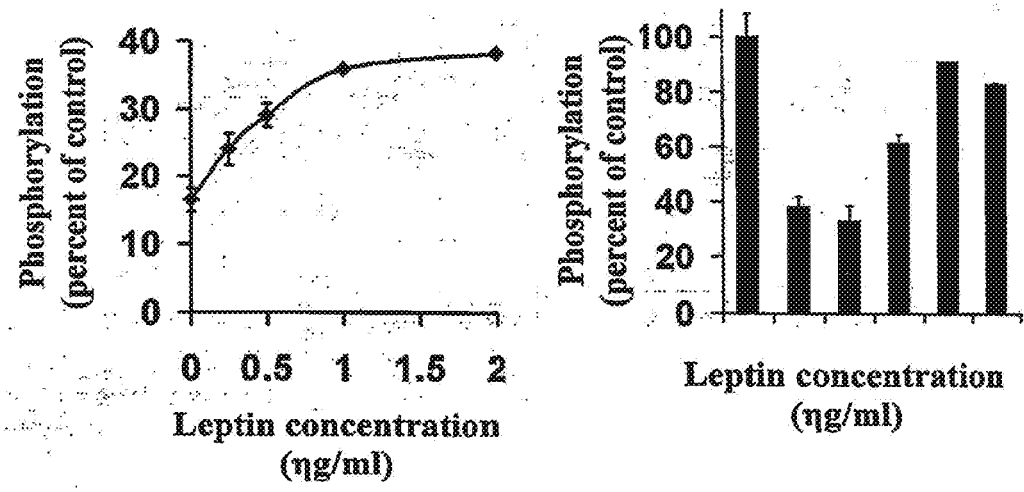

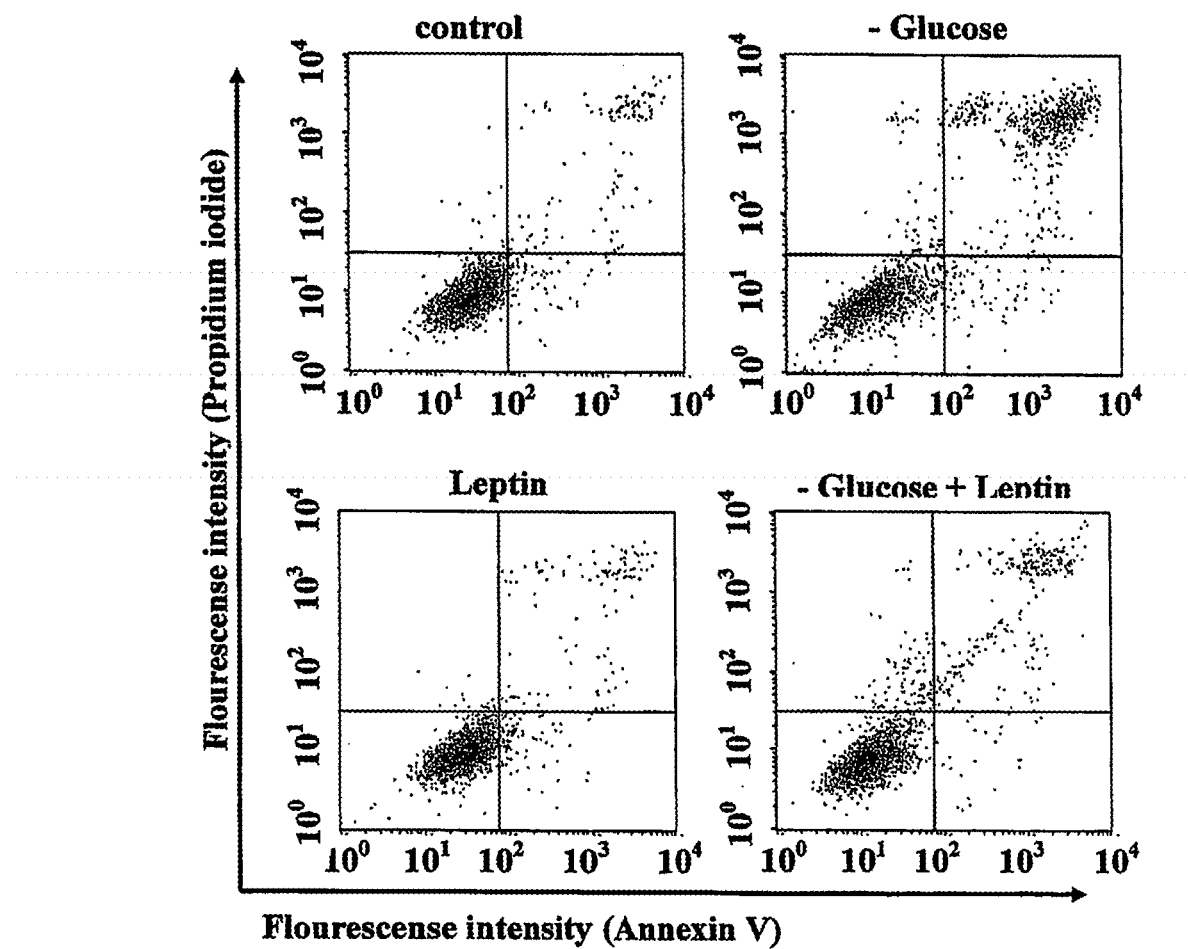

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthesised primer DNA

<400> SEQUENCE: 1
gatgttccaa accccaagaa                                                      20

<210> SEQ ID NO 2
<211> LENGTH: 20
<212> TYPE: DNA
<213> ORGANISM: Artificial Sequence
<220> FEATURE:
<223> OTHER INFORMATION: Synthesized DNA primer

<400> SEQUENCE: 2
atctgccggt gtgagttttc                                                      20

<210> SEQ ID NO 3
<211> LENGTH: 17
<212> TYPE: DNA
<213> ORGANISM: Artificial Sequence
<220> FEATURE:
<223> OTHER INFORMATION: Synthesized DNA primer

<400> SEQUENCE: 3
ctgagctgac ctggagc                                                         17

<210> SEQ ID NO 4
<211> LENGTH: 20
<212> TYPE: DNA
<213> ORGANISM: Artificial Sequence
<220> FEATURE:
<223> OTHER INFORMATION: Synthesized DNA primer

<400> SEQUENCE: 4
gacagaagat catgccgtcc                                                      20

<210> SEQ ID NO 5
<211> LENGTH: 20
<212> TYPE: DNA
<213> ORGANISM: Artificial Sequence
<220> FEATURE:
<223> OTHER INFORMATION: Synthesized DNA primer

<400> SEQUENCE: 5
cagcttcttt gcagctcctt                                                      20

<210> SEQ ID NO 6
<211> LENGTH: 20
<212> TYPE: DNA
<213> ORGANISM: Artificial Sequence
```

-continued

```
<220> FEATURE:
<223> OTHER INFORMATION: Synthesized DNA primer

<400> SEQUENCE: 6
catagctgct gggaccatct                                                      20

<210> SEQ ID NO 7
<211> LENGTH: 20
<212> TYPE: DNA
<213> ORGANISM: Artificial Sequence
<220> FEATURE:
<223> OTHER INFORMATION: Synthesized DNA primer

<400> SEQUENCE: 7
ccagtctctt gctcctcacc                                                      20

<210> SEQ ID NO 8
<211> LENGTH: 19
<212> TYPE: DNA
<213> ORGANISM: Artificial Sequence
<220> FEATURE:
<223> OTHER INFORMATION: Synthesized DNA primer

<400> SEQUENCE: 8
gactccagcc acaaagatg                                                       19

<210> SEQ ID NO 9
<211> LENGTH: 20
<212> TYPE: DNA
<213> ORGANISM: Artificial Sequence
<220> FEATURE:
<223> OTHER INFORMATION: Synthesized DNA primer

<400> SEQUENCE: 9
ggtaccaatg gcacttcaag                                                      20

<210> SEQ ID NO 10
<211> LENGTH: 19
<212> TYPE: DNA
<213> ORGANISM: Artificial Sequence
<220> FEATURE:
<223> OTHER INFORMATION: Synthesized DNA primer

<400> SEQUENCE: 10
tcacccacat aggagtcct                                                       19
```

COMPOUNDS FOR IMPROVING NUTRITIONAL STATUS, COGNITION AND SURVIVAL

This application is the U.S. national phase of International Application No. PCT/IL2006/001087, filed 14 Sep. 2006, which designated the U.S. and claims benefit to U.S. Provisional Application No. 60/717,247, filed 16 Sep. 2005, the entire contents of each of which are hereby incorporated by reference.

FIELD OF THE INVENTION

The present invention concerns compounds that improve nutritional status, well being and cognition functions, especially impaired cognition caused by malnutrition and prolong survival.

BACKGROUND OF THE INVENTION

Since the Garden of Eden and the trees of knowledge and life, the connection between food, cognition and survival has been recognized. Today, nutritional status is a well-accepted regulator of neural function and longevity.

Studies have shown that mild energy restriction (to 60% of control) improves cognitive function while severe restriction (to 40%) prejudices it. Such cognitive dysfunction may manifest as deficits in hippocampal-dependent learning and memory, including spatial information processing. The benefits of mild energy restriction have been repeatedly demonstrated in prolonging longevity and in improving neurodegenerative diseases. Understanding of the mechanisms for neural damage advanced when apoptosis was shown to be responsible for some of the neural cell loss found in Parkinson's and in Alzheimer's disease. Neuroapoptotic cell death is a multi-step process involving several key molecules, modulation of which may inhibit the process. Such neuroprotective agents were also found to overcome poor behavioral performance found in animal models for these diseases[1,2].

The mammalian forebrain contains populations of cells that divide and differentiate into neurons and glia. These neurons are generated continuously from stem cells in specific regions of the adult brain. Such constitutive neurogenesis can be modulated by changes in diet. Reduced nutritional status in mice increased the numbers of newly generated cells primarily in the dentate gyrus of the hippocampus[3,4], which is the principal center for learning and memory[5]; suppression of neurogenesis led to impaired learning and memory[6].

Cellular energy status is monitored and controlled by the 5'-AMP-activated protein kinase (AMPK) system. AMPK and its homologue in *Saccharomyces cerevisiae* are allosterically activated by 5'-AMP, which accumulates following ATP hydrolysis. 5'-AMP may also promote phosphorylation and activation of AMPK by an upstream kinase. Conversely, high ATP antagonizes the activating effects of 5'-AMP on AMPK. Stresses such as hypoxia, heat shock, metabolic poisoning and exercise, all activate AMPK by their effect on the ratio of 5-AMP to ATP. AMPK, in turn, phosphorylates multiple targets, which switch off anabolic pathways and stimulate catabolic ones[7]. Recent studies have demonstrated that this activation regulates intracellular signaling pathways involved in cellular survival and apoptotic cell death in endothelial cells, liver, pancreatic beta cells and other tissues[8,9,10]. AMPK is considered to act as a "fuel gauge" for cellular metabolism, controlling the endogenous energy supply of ATP. It was not surprising therefore, when AMPK was also found to regulate feeding behavior[11,12].

Leptin is an adipokine hormone that plays a central role in food intake, energy balance and body weight regulation, mainly through its hypothalamic receptors[13,14,15]. Studies on leptin function have demonstrated that AMPK is essential for mediating its actions[16]. While leptin exerts its catabolic effects in the periphery by stimulating AMPK phosphorylation and activation, its central effects on energy balance act through hypothalamic AMPK dephosphorylation and inhibition[11,12].

There are also leptin receptors in the hippocampus but its role in memory learning and cognitive functions has never been elucidated.

SUMMARY OF THE INVENTION

While reducing the present invention to practice, the inventors used diet restriction (DR) tools to define the processes underlying the effects of nutrition on cognition and survival. Their results indicate that AMP kinase responds to nutritional status and modulates cognitive ability by affecting the balance between neurogenesis and neuroapoptosis. Leptin reverses the deleterious effects of severe DR.

By one aspect, termed "the nutritional stress aspect" the present invention concerns a method for treating undesirable manifestations of a nutritional stress condition comprising: administering to a subject in need of such treatment a therapeutically effective amount of a leptin receptor agonist or an activator of the AMPK signal transduction pathway.

The present invention further concerns use of a leptin receptor agonist or an activator of the AMPK signal transduction pathway for the preparation of a medicament for the treatment of undesirable manifestations of a nutritional stress condition.

The present invention further concerns a pharmaceutical composition for the treatment of undesirable manifestations of a nutritional stress condition comprising a pharmaceutically acceptable carries and as an active ingredient a leptin receptor agonist or an activator of the AMPK signal transduction pathway.

The term "leptin receptor agonist" refers to one of the following:
(a) a leptin protein, a fragment of a leptin protein having physiological properties of the leptin protein, variant leptin protein or variant of a fragment of a leptin protein fragment, having physiological properties of the leptin protein;
(b) a leptin receptor agonist being a leptin mimic;
(c) a combination of two or more of (a)-(b).

The present invention further concerns a method for treating undesirable manifestations of a nutritional stress condition comprising: administering to a subject in need of such treatment a therapeutically effective amount of an agent selected from:
(a) a leptin protein; a fragment of a leptin protein having physiological properties of the leptin protein; variant leptin protein or variant of a fragment of a leptin protein fragment having physiological properties of the leptin protein;
(b) a leptin receptor agonist being a leptin mimic;
(c) an activator of the AMPK signal transduction pathway;
(d) a combination of two or more of (a)-(c).

The present invention further concerns use of an agent selected from:
(a) a leptin protein; a fragment of a leptin protein having physiological properties of the leptin protein; variant leptin protein or variant of a fragment of a leptin protein fragment having physiological properties of the leptin protein;
(b) a leptin receptor agonist being a leptin mimic;
(c) an activator of the AMPK signal transduction pathway;
(d) a combination of two or more of (a)-(c).
for the preparation of a medicament for the treatment of undesirable manifestations of a nutritional stress condition.

The present invention further concerns a pharmaceutical composition for the treatment of undesirable manifestations of a nutritional stress condition comprising a pharmaceutically acceptable carries and as an active ingredient an agent selected from:
(a) a leptin protein; a fragment of a leptin protein having physiological properties of the leptin protein; variant leptin protein or variant of a fragment of a leptin protein fragment having physiological properties of the leptin protein;
(b) a leptin receptor agonist being a leptin mimic;
(c) an activator of the AMPK signal transduction pathway;
(d) a combination of two or more of (a)-(c).

By another aspect, termed "improved cognitive aspect" the present invention concerns a method for improving cognitive function comprising: administering to a subject in need of such treatment a therapeutically effective amount of a leptin receptor agonist or an activator of the AMPK signal transduction pathway.

The present invention further concerns use of a leptin receptor agonist or an activator of the AMPK signal transduction pathway for the preparation of a medicament for improving cognitive function.

The present invention further concerns a pharmaceutical composition for improving cognitive function comprising a pharmaceutically acceptable carries and as an active ingredient a leptin receptor agonist or an activator of the AMPK signal transduction pathway.

The term "leptin receptor agonist" refers to one of the following:
(a) a leptin protein, a fragment of a leptin protein having physiological properties of the leptin protein, variant leptin protein or variant of a fragment of a leptin protein fragment having physiological properties of the leptin protein;
(b) a leptin receptor agonist being a leptin mimic;
(c) a combination of two or more of (a)-(b).

The present invention further concerns a method for improving cognitive function comprising: administering to a subject in need of such treatment a therapeutically effective amount of an agent selected from:
(a) a leptin protein; a fragment of a leptin protein having physiological properties of the leptin protein; variant leptin protein or variant of a fragment of a leptin protein fragment having physiological properties of the leptin protein;
(b) a leptin receptor agonist being a leptin mimic;
(c) an activator of the AMPK signal transduction pathway;
(d) a combination of two or more of (a)-(c).

The present invention further concerns use of an agent selected from:
(a) a leptin protein; a fragment of a leptin protein having physiological properties of the leptin protein; variant leptin protein or variant of a fragment of a leptin protein fragment having physiological properties of the leptin protein;
(b) a leptin receptor agonist being a leptin mimic;
(c) an activator of the AMPK signal transduction pathway;
(d) a combination of two or more of (a)-(c).
for the preparation of a medicament for improving cognitive function.

The present invention further concerns a pharmaceutical composition for improving cognitive function comprising a pharmaceutically acceptable carries and as an active ingredient an agent selected from:
(a) a leptin protein; a fragment of a leptin protein having physiological properties of the leptin protein; variant leptin protein or variant of a fragment of a leptin protein fragment having physiological properties of the leptin protein;
(b) a leptin receptor agonist being a leptin mimic;
(c) an activator of the AMPK signal transduction pathway;
(d) a combination of two or more of (a)-(c).

The following definitions are relevant to the first aspect of the invention concerning the "nutritional stress aspect"

The term "nutritional stress condition" refers to any condition caused by acute or chronic negative energy balance. These conditions include: sepsis, prolonged post-surgical stress, prolonged post injury stress, brain damage caused by liver disease; and the weight loss associated with severe malnutrition found in developing countries, mal-absorption conditions such as celiac disease, colitis, carbohydrate intolerance that can lead to chronic malnutrition, malnutrition caused by chronic diseases such as cancer or infection in general and HIV infection in particular, anorexia. All these conditions typically need nutritional rehabilitation.

The term "undesirable manifestation" refers to any clinical or behavioral pathology which is associated with the nutritional stress conditions. These include decrease in cognitive function especially a decrease associated with chronic or acute malnutrition, apathy and fatigue, lack of energy, slowness of healing of tissue, decreased rates of recovery (from surgery), decrease growth rates (in children), increases mortality, decrease in immune system function, increased susceptibility to infection, decreased fertility. Preferably in accordance with the invention the method if for the treatment of impaired cognitive function (notably learning and memory) associated with the nutritional stress condition. In accordance with a preferred embodiment the undesirable manifestation is a decrease in cognitive function.

The term "treatment" in the context of the first "nutritional stress aspect" of the invention refers to the improvement of at least one parameter of the "undesirable manifestation" as compared to a non-treated control. This term refers both to the improvement of an established pathology (improvement in a pre-existing undesirable manifestation, such as impaired cognitive function, cause by the chronic or acute malnutrition), as well as to the prevention of the occurrence of the pathology altogether before it occurs, or prevention of the undesirable manifestation development to the full extent as compared to the non-treated control. For example, a patient which is expected to go into a nutritional stress condition (due to an operation, due to predicted deterioration in his cancer of HIV disease) may receive the treatment of the invention in order to prevent, or at least decrease, the undesirable manifestation before it occurred (or before it develops to a severe undesired manifestation), notably to prevent or diminish the decrease in the cognitive function associated with the nutritional stress condition.

The following are the definition in connection with the second aspect "improved cognitive function aspect" of the invention The term "cognitive function" refers in general to learning and memory capacities.

The "improvement in cognitive function" may be any improvement in learning or memory capacities as compared to untreated control, or the slowing down or prevention in the deterioration of the cognitive function as compared to the untreated control.

The patient in connection with the aspect of improvement of cognitive function may be an patient which cognitive function deteriorated due to aging, infection, due to stroke, due to brain damage caused by liver disease, to neurodegenerative disease such as Alzheimer's, Parkinson, Huntington Chorea, other neurodegenerative processes associated with dementia and cachexia, preferably cognitive impairment accompanied by weight loss.

The following definitions are relevant to both aspects of the invention:

The term "administration" refers to any type of systemic administration and may include all parenteral administrations such as intravenous, subcutaneous, intramuscular, intaperitoneal by intranasal (to enhance penetration to the brain), depo administration (for slow release), inhalation, oral.

Preferred modes of administration are subcutenous, inhalation, intaperitoneal by intranasal.

The term "therapeutically effective amount" refers to an amount sufficient to bring about the decrease, prevention or elimination of the undesirable manifestation of any of the agents mentioned in (a) to (d) above. It should be noted that, when the active agent is an agent capable of activating the AMPK signal transduction pathway, the therapeutically effective amount should be an amount that causes low level activation of the pathway, as only low-level activation results in neurogenesis while higher level activation may result in the opposite effect—apoptosis of neurons.

In order to determine what is "low level activation" varying doses of the AMPK pathway activator may be administered to test animals in the final formulation intended to be used in humans, together with Brd-U. Animals are than sacrificed and the number of BrdU-immunoreactive cells in the dentate gyrus is determined in order to measure the generation rate of new cells. Amounts that are capable of increasing the number of newly generated cells are considers as "therapeutically effective amounts" when converted, according to known criteria, to physiologically corresponding amounts in humans. The Active Agents Used in the Method of the Invention May be:

The full leptin protein having a sequence as shown in Zhang Y, Proenca R, Maffei M, Barone M, Leopold L, Friedman J M. Positional cloning of the mouse obese gene and its human homologue. Nature 1994 1:372 (6505):425-432. and as indicated in GeneBank accession number u43653.

According to a preferred embodiment of the invention this is the preferred aspect Instead of the full protein a fragment of the protein it is possible to use the fragment or a variant (of the full protein or the receptor) having a physiological properties similar (in the same concentration range) as the parent leptin protein.

Instead of the full protein or fragment, variants may be used in which one or more amino acids have been replaced by another amino acid (naturally occurring or synthetic) in a conservative or non-conservative substitution, variants in which one or more non-terminal amino acids have been deleted; variants in which one or more amino acids have been chemically modified or variants wherein the bonds between amino acids has been replaced to a non-naturally occurring bond. The variants should be those still maintain the physiological leptin receptor activation properties of the full parent protein.

The variants may also be obtained by adding various peptidic or non-peptidic moieties to the leptin, leptin fragment or leptin variants for example in order to enhance its penetration (to the BBB), to decrease its clearance rate, to improve its release rates, to improve its solubility, bioavailability, immunological properties, pharmacokinetic properties etc.

For determining whether the fragment of the variant maintains the properties of the parent leptin it is possible to test them in an assay such as:
1) Activation of the leptin receptor (by RT-PCR, receptor binding)
2) Prolonging animal survival under severe caloric restriction;
3) Test of cognitive functions such as Eight Arm Maze which will be stipulated below; or the Morris water maze test;
4) Preventing apoptosis from cultured neurons (under stress conditions) as compared to control
5) Determining AMPK expression and phosphorylation.

Fragments and variants which are active in any one of the above 5 assays in a concentrations which are not significantly less that that of the full leptin are those the fall under the scope of the present invention.

The agent in accordance with the invention may also be a leptin receptor agonist being a leptin mimic (a molecule which is not a protein) such as CBT1452 (Cambridge Biotechnology Ltd), {D-LEU-4}-OB3 Grasso P (Regul Pept. 2001 Sep. 15; 101(1-3):123-9.);

Another agent for use in the method of the invention are agents that activate the AMPK signal transduction pathway which include agent that activate the AMPK itself, its upstream effectors such as TSC2 as well as downstream elements such as LKB1. An example of a AMPK activator is AICAR, metformin Additional possible targets for AMPK are shown in FIG. 6

DESCRIPTION OF THE DRAWINGS

FIG. 3. Nutritional status modulates leptin level and receptors. Mice were kept under diet restriction for 10 days and serum leptin was evaluated by ELISA (A). Top broken line represents control group, the bottom broken one 60% DR and the continuous line 40% DR (B) RT-PCR analysis of the long and the short form of the OB receptors. (C) Mice were diet restricted and injections of 1 mg/kg leptin. AMPK expression and phosphorylation was analyzed by immunoblotting.

FIG. 6 Shows downstream targets for AMPK.

FIG. 8 Cell survival and neuroprotection after leptin administration. Cultured cardiomyocytes exposed to glucose deprivation for 1, 3, 6 h were treated with leptin. Stat-3 phosphorylation (A) and AKT phosphorylation (measure of cell survival and cardioprotection) were measured by protein analysis.

FIG. 9. Leptin decreased apoptosis following nutritional stress. Cultured cardiomyocytes exposed to glucose deprivation, and treated with 1 ug/ml leptin. Apoptosis was analyzed by a FACS FIG. 10. Leptin reversed activity to control level in an experimental model of Hepatic Encephalopathy. Mice were treated with TAA, then 1 mg/kg Leptin was administrated daily for 5 days and activity index was evaluated.

DETAILED DESCRIPTION OF THE INVENTION

Figure 1A:
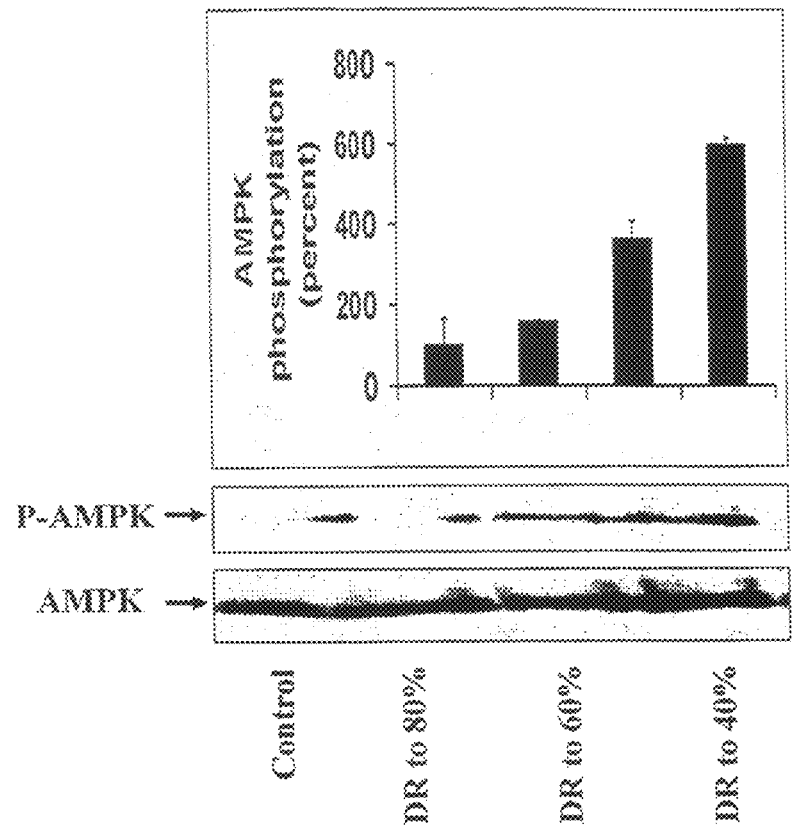
FIG. 1. Diet restriction induces neuronal AMPK activation in-vivo. (A) Mice were diet restricted to 80%, 60% and 40%. AMPK expression and phosphorylation was analyzed by immunoblotting. (B) BrdU+ cells in the granule cell layer and in the sub granular zone of the dentate gyrus were photographed using a fluorescent microscope. (C) Mice were treated with or without 25 nM AICAR and then tested in an eight-arm maze. Solid lines represent the control group and the broken line the treated group. (D) The effect of AICAR on catecholamine concentrations. (E) Mice were treated with 1-2 mM AICAR and performance in the eight-arm maze was compared to control and 40% DR. (F) Bcl-2 and Bax level were analyzed by RT-PCR and immunoblotting. Black columns represent Bcl-2 protein and the hatched columns Bax.

The full leptin is a sequence of 146 amino acids peptide. The term "fragment" refers to any continuous section, preferably of at least 7, at least 8, at least 9, at least 10, at least 11, at least 12, at least 13 at least 14, at least 15 amino acids.

The term "variant" refers to a full leptin protein or to a fragment as defined above wherein up to 40%, preferably, up to 35%, 30%, 25%, 20%, 15%, 10, or 5% of amino acids of the native sequence have been replaced with a naturally or non-naturally occurring amino acid or with a peptidomimetic organic moiety. This means that the variant in accordance with the present invention, concerns an amino acid sequence, which shares (is homologous) at least 60% (preferably 65%, 70%, 75%, 80%, 85%, 90%, 95%, 96%, 97%, 98% or 99%) of its amino acid with the native sequence, but some of the amino acids were replaced either by other naturally occurring amino acids, (both conservative and non-conservative substitutions), by non-naturally occurring amino acids (both conservative and non-conservative substitutions), or with organic moieties which serve either as true peptidomimetics (i.e., having the same steric and electrochemical properties as the replaced amino acid), or merely serve as spacers in lieu of an amino acid, so as to keep the spatial relations between the amino acid spanning this replaced amino acid. Guidelines for the determination of the replacements and substitutions are given below. Preferably no more than 30%, 25%, 20% or 10% of the amino acids are replaced.

The term "variant" may also include amino acids where up to 40% of the amino acids (preferably, up to 35%, 30%, 25%, 20%, 15%, 10, or 5%) have their side chains chemically modified. These modifications refer to a variant which has the same type of amino acid residue, but to its side chain a functional group has been added. For example, the side chain may be phosphorylated, glycosylated, fatty acylated, acylated, iodinated or carboxyacylated. Other examples of chemical substitutions are known in the art.

The term "variant" also refers to the protein where some amino acids (non-terminal and not necessarily continuous stretch of amino acids) have been deleted, preferably no more than up to 20% (preferably 15%, 10%, 5%) of the amino have been deleted.

Typically the variant is such that least 50% (preferably at least 55%, 60%, 70%, 75%, 80%, 85%, 90%, 95%) of the amino acids in the parent leptin protein are maintained unaltered in the variants. This means that up to 40% substitution, up to 40% chemical modification and up to 20% deletions are combinatorial, i.e., the same variant may have substitutions, chemical modifications and deletions so long as at least 50% of the native amino acids are identical to those of the native sequence of the leptin protein both as regards the nature of the amino acid residue and its position in the sequence. In addition, the physiological properties of the parent sequence, in either improving undesirable manifestations of malnutrition according to the first aspect of the invention or improving cognitive function under the second aspect of the invention signal transduction, have to be maintained in the variant typically, at the same or higher concentration.

Typically "essential amino acids" are maintained or replaced by conservative substitutions while non-essential amino acids may be maintained, deleted or replaced by conservative or non-conservative replacements. Generally, essential amino acids are determined by various Structure-Activity-Relationship (SAR) techniques (for example amino acids when replaced by Ala cause loss of activity) are replaced by conservative substitution while non-essential amino acids can be deleted or replaced by any type of substitution. Guidelines for the determination of the deletions, replacements and substitutions are given below.

The variant may also include a peptide in which at least one peptidic backbone has been altered to a non-naturally occurring peptidic backbone". This variant includes at least one bond between the N— of one amino acid residue to the C— of the next has been altered to non-naturally occurring bonds by reduction (to —$CH_2$—NH—), alkylation (methylation) on the nitrogen atom, or the bonds have been replaced by amidic bond, urea bonds, or sulfonamide bond, etheric bond (—$CH_2$—O—), thioetheric bond (—$CH_2$—S—), or to —CS—NH—; The side chain of the residue may be shifted to the backbone nitrogen to obtain N-alkylated-Gly (a peptidoid).

The variant may also be a full leptin protein, fragment or previously described variants where various functional groups were added to one or both of its terminals. The purpose of such a functional group may be for the improvement of the physiological properties notably to improve bioavailability and entrance through the blood brain barrier. Thus functional groups that are known to promote BBB penetration may be complexed (preferably by a cleavable bond) to any of the active agents of the invention). The functional groups may also other purposes such as improvement in stability, penetration (through cellular membranes or barriers), tissue localization, efficacy, decreased clearance, decreased toxicity, improved selectivity, improved resistance to repletion by cellular pumps, and the like.

Suitable functional groups are described in Green and Wuts, "*Protecting Groups in Organic Synthesis*", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds these being an example for "a moiety for transport across cellular membranes".

These moieties can be cleaved in vivo, either by hydrolysis or enzymatically, inside the cell. (Ditter et al., *J. Pharm. Sci.* 57:783 (1968); Ditter et al., J. Pharm. Sci. 57:828 (1968); Ditter et al., J. Pharm. Sci. 58:557 (1969); King et al., *Biochemistry* 26:2294 (1987); Lindberg et al., *Drug Metabolism and Disposition* 17:311 (1989); and Tunek et al, *Biochem. Pharm.* 37:3867 (1988), Anderson et al., *Arch. Biochem. Biophys.* 239:538 (1985) and Singhal et al., *FASEB J.* 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a compound of the present invention is protected, preferably with a methyl, ethyl, benzyl or substituted benzyl ester, more preferably as a benzyl ester.

In addition, a modified lysine residue can be added to the C-terminal of the compound to enhance biological activity. Examples of lysine modification include the addition of an aromatic substitute, such as benzoyl benzoic acid, dansyl-lysine various derivatives of benzoic acids (difluoro-, trifluoromethyl-, acetamido-, dimethyl-, dimethylamino-, methoxy-) or various derivatives of carboxylic acid (pyrazine-, thiophene-, pyridine-, indole-, naphthalene-, biphenyl,), or an aliphatic group, such as acyl, or a myristic or stearic acid, at the epsilon amino group of the lysine residue.

Examples of N-terminal protecting groups include acyl groups (—CO—$R_1$) and alkoxy carbonyl or aryloxy carbonyl groups (—CO—O—$R_1$), wherein $R_1$ is an aliphatic, substituted aliphatic, benzyl, substituted benzyl, aromatic or a substituted aromatic group. Specific examples of acyl groups include acetyl, (ethyl)-CO-n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO— Examples of alkoxy carbonyl and aryloxy carbonyl groups include $CH_3$—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoyl, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —$NH_2$, —$NHR_2$ and —$NR_2R_3$) or ester (i.e., the hydroxyl group at the C-terminus is replaced with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —N(ethyl)$_2$, —N(methyl)(ethyl), —NH(benzyl), —N(C1-C4 alkyl)(benzyl), —NH(phenyl), —N(C1-C4 alkyl) (phenyl), —$OCH_3$, —O-(ethyl), —O-(n-propyl), —O-(n-butyl), —O-iso-propyl), —O-(sec-butyl), —O-(t-butyl), —O-benzyl and —O-phenyl.

Preferably the compounds includes in the N-terminal a hydrocarbon having a length of $C_4$-$C_{20}$ preferably $C_6$-$C_{18}$, most preferably $C_8$-$C_{16}$. Example of hydrophobic moieties are: aaystyl, stearyl, lauroyl, palmitoyl and acetyl etc. Other examples are gernyl-gernyl, acetyl.

In order to determine where to replace, delete or chemically modify amino acids of the lepton protein or which fragment can be chosen it is important to identify essential and non-essential amino acids. This can be done in one of the following:

Ala-Scan

Essential amino acids have to be maintained (i.e., be identical to those appearing in the native leptin) chemically modified or replaced by conservative substitutions (see definition below) to obtain variants or the fragments of the invention. Non-essential amino acids can be maintained, deleted, replaced by a spacer or replaced by conservative or non-conservative substitutions.

Identification of essential vs. non-essential amino acids in the peptide can be achieved by preparing several peptides in which each amino acid is sequentially replaced by the amino acid Ala ("Ala-Scan"), or sequentially each amino acid is omitted ('omission-scan"). This allows to identify the amino acids which modulating activity is decreased by said replacement/omission ("essential") and which are not decreased by said replacement/omission ("non-essential") (Morrison et al., *Chemical Biology* 5:302-307, 2001). Another option for testing the importance of various peptides is by the use of site-directed mutagenesis. Other Structure-Activity-Relationship techniques may also be used.

3D-Analysis

Another strategy for finding essential vs. non-essential amino acids is by determining which aa of the region, in the 3D of the full leptin, are exposed and which are cryptic. This can be done using standard software such as SPDB viewer, "color by accessibility" of Glaxo-Welcome.

Typically cryptic aa are non-essential and exposed or partially exposed amino acids are more likely to be essential. However, if one wishes to "guess" theoretically which "non-conservative" substitutions in the cryptic region can be tolerated, a good guideline is to "check" on a 3D computer model of the full leptin Those non-conservative substitution, that when simulated on a computer's 3D structure (for example using the Triphose™ software) do not cause drastic alteration of the overall shape of the region (drastic shifting in the position of the exposed amino acids) are likely non-conservative replacements. Thus prior to experimental testing it is possible to reduce the number of tested candidates by computer simulation. Where the 3D structure of a specific kinase is not available in activating crystallography data, it is possible to obtain a "virtual" 3D structure of the kinase based on homology to known crystallographic structures using such progress such as CompSer™ (Tripose, USA).

Deletions can occur in particular of the "non-essential amino acids". Additions may occur in particular at the N-terminal or the C-terminal of any of the amino acids of the sequence. No more than 20%, preferably 15%. 10%, 5% of the amino acids should be deleted. Insertions should preferably be N-terminal or C-terminal to the sequence of the peptide/fragments/variants. However other insertions or deletions are possible.

Replacements

The variants can be obtained by replacement of any of the amino acids as present in the native leptin. As may be appreciated there are positions in the sequence that are more tolerant to substitutions than others, and in fact some substitutions may improve the activity of the native sequence. The determination of the positions may be realized using "Ala-Scan," "omission scan" "site directed mutagenesis" or 3-D theoretical considerations as described above. Generally speaking the amino acids which were found to be "essential" should either be identical to the amino acids present in the native leptin or alternatively substituted by "conservative substitutions". The amino acids that were found to be "non-essential" might be identical to those in the native peptide, may be substituted by conservative or non-conservative substitutions, and may be deleted or replaced by a "spacers".

The term "naturally occurring amino acid" refers to a moiety found within a peptide and is represented by —NH—CHR—CO—, wherein R is the side chain of a naturally occurring amino acid.

The term "non-naturally occurring amino acid" (amino acid analog) is either a peptidomimetic, or is a D or L residue having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. This term also refers to the D-amino acid counterpart of naturally occurring amino acids. Amino acid analogs are well known in the art; a large number of these analogs are commercially available. Many times the use of non-naturally occurring amino acids in the peptide has the advantage that the peptide is more resistant to degradation by enzymes which fail to recognize them.

The term "conservative substitution" in the context of the present invention refers to the replacement of an amino acid present in the native sequence of the leptin with a naturally or non-naturally occurring amino or a peptidomimetics having similar steric properties.

As the naturally occurring amino acids are grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The following are some non-limiting examples of groups of naturally occurring amino acids or of amino acid analogs are listed bellow. Replacement of one member in the group by another member of the group will be considered herein as conservative substitutions:

Group I includes leucine, isoleucine, valine, methionine, phenylalanine, serine, cysteine, threonine and modified amino acids having the following side chains: ethyl, n-butyl, —$CH_2CH_2OH$, —$CH_2CH_2CH_2OH$, —$CH_2CHOHCH_3$ and —$CH_2SCH_3$. Preferably Group I includes leucine, isoleucine, valine and methionine.

Group II includes glycine, alanine, valine, serine, cysteine, threonine and a modified amino acid having an ethyl side chain. Preferably Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, CO—NH-alkylated glutamine or asparagine (e.g., methyl, ethyl, n-propyl and iso-propyl) and modified amino acids having the side chain —$(CH_2)_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, glutamine, asparagine, methyl aspartate, ethyl aspartate, benzyl aspartate and methyl glutamate, ethyl glutamate and benzyl glutamate.

Group V includes histidine, lysine, arginie, N-nitroarginine, β-cycloarginine, μ-hydroxyarginine, N-amidinocitruline and 2-amino-4-guanidinobutanoic acid, homologs of lysine, homologs of arginine and ornithine. Preferably, Group V includes histidine, lysine, arginine, and ornithine. A homolog of an amino acid includes from 1 to about 3 additional methylene units in the side chain.

Group VI includes serine, threonine, cysteine and modified amino acids having C1-C5 straight or branched alkyl side chains substituted with —OH or —SH. Preferably, Group VI includes serine, cysteine or threonine.

In this invention any cysteine in the original sequence or subsequence can be replaced by a homocysteine or other sulfhydryl-containing amino acid residue or analog. Such analogs include lysine or beta amino alanine, to which a cysteine residue is attached through the secondary amine yielding lysine-epsilon amino cysteine or alanine-beta amino cysteine, respectively.

The term "non-conservative substitutions" concerns replacement of the amino acid as present in the native Lyn by another naturally or non-naturally occurring amino acid, having different electrochemical and/or steric properties, for example as determined by the fact the replacing amino acid is not in the same group as the replaced amino acid of the native kinase sequence. Those non-conservative substitutions which fall under the scope of the present invention are those which still constitute a compound having kinase-associated signal transduction modulating activities. Because D-amino acids have hydrogen at a position identical to the glycine hydrogen side-chain, D-amino acids or their analogs can often be substituted for glycine residues, and are a preferred non-conservative substitution.

A "non-conservative substitution" is a substitution in which the substituting amino acid (naturally occurring or modified) has significantly different size, configuration and/or electronic properties compared with the amino acid being substituted. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or—

"Peptidomimetic organic moiety" can be substituted for amino acid residues in the compounds of this invention both as conservative and as non-conservative substitutions. These peptidomimetic organic moieties either replace amino acid residues of essential and non-essential amino acids or act as spacer groups within the peptides in lieu of deleted amino acids (of non-essential amino acids). The peptidomimetic organic moieties often have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the compounds retain their leptin-like physiological properties as compared to compounds constituting sequence regions identical to those appearing in the native leptin protein.

Peptidomimetics are often used to inhibit degradation of the peptides by enzymatic or other degradative processes. The peptidomimetics can be produced by organic synthetic techniques. Examples of suitable peptidomimetics include D amino acids of the corresponding L amino acids, tetrazol (Zabrocki et al., *J. Am. Chem. Soc.* 110:5875-5880 (1988)); isosteres of amide bonds (Jones et al., Tetrahedron Lett. 29: 3853-3856 (1988));

LL-3-amino-2-propenidone-6-carboxylic acid (LL-Acp) (Kemp et al., *J. Org. Chem.* 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., *J. Org. Chem.* 54:109-115 (1987). Other suitable peptidomimetics are shown in Nagai and Sato, Tetrahedron Lett. 26:647-650 (1985); Di Maio et al., *J. Chem. Soc. Perkin Trans.,* 1687 (1985); Kahn et al., Tetrahedron Lett. 30:2317 (1989); Olson et al., *J. Am. Chem. Soc.* 112:323-333 (1990); Garvey et al., *J. Org. Chem.* 56:436 (1990). Further suitable peptidomimetics include hydroxy-1,2,3,4-tetrahydroisoquinoline-3-carboxylate (Miyake et al., *J. Takeda Res. Labs* 43:53-76 (1989)); 1,2,3, 4-tetrahydro-isoquinoline-3-carboxylate (Kazmierski et al., *J. Am. Chem. Soc.* 133:2275-2283 (1991)); histidine isoquinolone carboxylic acid (HIC) (Zechel et al., *Int. J. Pep. Protein Res.* 43 (1991)); (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett. (1991)).

In the present invention the side amino acid residues appearing in the native sequence may be chemically modified, i.e., changed by addition of functional groups. The modification may be in the process of synthesis of the molecule, i.e., during elongation of the amino acid chain and amino acid, i.e., a chemically modified amino acid is added. However, chemical modification of an amino acid when it is present in the molecule or sequence ("in situ" modification) is also possible.

The amino acid of any of the sequence regions of the molecule can be modified (in the peptide conceptionally viewed as "chemical modified") by carboxymethylation, acylation, phosphorylation, glycosylation or fatty acylation. Ether bonds can be used to join the serine or threonine hydroxyl to the hydroxyl of a sugar. Amide bonds can be used to join the glutamate or aspartate carboxyl groups to an amino group on a sugar (Garg and Jeanloz, Advances in *Carbohydrate Chemistry and Biochemistry*, Vol. 43, Academic Press (1985); Kunz, *Ang. Chem. Int.* Ed. English 26:294-308 (1987)). Acetal and ketal bonds can also be formed between amino acids and carbohydrates. Fatty acid acyl derivatives can be made, for example, by free amino group (e.g., lysine) acylation (Toth et al., Peptides: *Chemistry, Structure and Biology*, Rivier and Marshal, eds., ESCOM Publ., Leiden, 1078-1079 (1990)).

The active protein, fragments and variants of the invention can be synthesized by solid phase synthesis, by expression in recombinant systems using suitable expression vectors or by isolation from natural source. Production by recombinant techniques being preferred.

The compounds of this invention can be synthesized utilizing a 430A Peptide Synthesizer from Applied Biosystems using F-Moc technology according to manufacturer's protocols. Other suitable methodologies for preparing peptides are known to person skilled in the art. See e.g., Merrifield, R. B., *Science,* 232: 341 (1986); Carpino, L. A., Han, G. Y., *J. Org. Chem.,* 37: 3404 (1972); Gauspohl, H., et al., *Synthesis,* 5: 315 (1992)). The teachings of which are incorporated herein by reference. Agents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980).

The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Preferably the agents of the invention, notably the full leptin protein are dissolved in water and administered in saline.

Pharmaceutical compositions can also include large, slowly metabolized macromolecules such as proteins, polysaccharides such as chitosan, polylactic acids, polyglycolic acids and copolymers (such as latex functionalized Sepharose™ agarose, cellulose, and the like), polymeric amino acids, amino acid copolymers, and lipid aggregates (such as oil droplets or liposomes).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. The compounds can be administered in the form of a depot injection or implant preparation which can be formulated in such a manner as to permit a sustained release of the active ingredient. An exemplary composition comprises monoclonal antibody at 5 mg/ml, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

As the compounds are to enter the blood brain barrier the formulations would be preferably those that can pass through the BBB. This can be achieved by nasal or ocular administration, by use of liposomes or particles which are known to be transported to the BBB, BBB administration can also be achieved by other strategies to go through the BBB may entail the use of endogenous transport systems, including carrier-mediated transporters such as glucose and amino acid carriers; receptor-mediated transcytosis for insulin or transferrin; and blocking of active efflux transporters such as p-glycoprotein.

The amount of the active agent of the invention should be determined in accordance with the mode of administration, the age, weight, sex of the patient, and the type and severity of the disease to be treated.

Generally the amount, when the full leptin protein is used varies between 0.02 mg/kg a day to 10 mg/kg a day, (preferably 0.028 mg/kg to 2 . . . mg/kg most preferably . . . 0.02. mg/kg. to 1 mg/kg a day Experimental Procedures
Cells and Reagents PC-12 cells were kindly provided by O. Meyuhas, Dept. of Biochem., Faculty of Medicine, Jerusalem. These cells were grown either in Dulbecco's modified Eagle's medium (DMEM) supplemented with 8% horse serum, 8% fetal bovine serum (FBS), glutamine, and gentamicin or with 1% horse serum, in the presence of nerve growth factor (NGF) (50 ng/ml), which causes the cells to differentiate. Murine leptin was provided by A. Gertler. AICAR was obtained from Toronto Research Chemicals (TRC).

Mice

The experimental protocol was approved by the institutional committee for the use of animals, No. MD-89.52-4. Eight to ten-week old female Sabra mice (29-32 g) were assigned at random to different groups of ten mice. The food provided was Purina chow.

Diet Restriction

Control mice received food ad-libitum. Diet-restricted mice received a diet of 57 kCal/week/mouse (2.16 g/day/mouse) as 60% of the requirement, or 38 kCal/week/mouse (1.44 g/day/mouse) for 40%/DR. DR was carried out for 10 days. Behavioral test was performed using the eight-arm spatial maze during the second week of experiment. During the behavioral tests, half of the animals in each group were injected intraperitoneally (i.p) with AICAR (1-2 mM equal to 258-516 mg/kg) or leptin (1 mg/kg) and the other half with saline. Mice were sacrificed by decapitation after the behavioral tests and the hippocampi were frozen at $-70°$ C.

RT-PCR Analysis

Total hippocampal RNA was extracted using TriFast reagent according to the manufacturer's instructions and reverse transcribed. Primers specific for OBRlong were GATGTTCCAAACCCCAAGAA (SEQ ID NO: 1) and CATAGCTGCTGGGACCATCT (SEQ ID NO: 6), for OBRshort ATCTGCCGGTGTGAGTTTTC (SEQ ID NO: 2), and CCAGTCTCTTGCTCCTCACC (SEQ ID NO: 7), for BAX CTGAGCTGACCTGGAGC (SEQ ID NO: 3) and GACTCCAGCCACAAAGATG (SEQ ID NO: 8) for Bcl-2 GACAGAAGATCATGCCGTCC (SEQ ID NO: 4) and GGTACCAATGGCACTTCAAG (SEQ ID NO: 9) and for actin CAGCTTCTTTGCAGCTCCTT (SEQ ID NO: 5) and TCACCCACATAGGAGTCCT (SEQ ID NO: 10). All primers were synthesized by Danyel Biotech.

Immunoblot Analysis

Total hippocampal Protein was extracted using TriFast reagent. Aliquots of the clarified lysates containing 30 mg protein were denatured in Laemmli sample buffer (6% SDS 30%, glycerol, 0.02% bromophenol blue, 200 mM Tris-HCl (pH 6.8), and 250 mM-mercaptoethanol, at 95° C. for 5 min. The samples were resolved by SDS-PAGE (10% acrylamide), and blotted onto nitrocellulose membrane. Non-specific binding in a Western blot analysis was prevented by immersing the membranes in blocking buffer (5% nonfat dry milk in Tris-buffer saline-Tween 20 (TBS-T)), for 2 h at room temperature. The membranes were then exposed to the indicated antibodies diluted 1:1000 for 1 h at room temperature. AMPK, phospho-AMPK and PARP were obtained from Cell Signaling. Bax, bcl-2 and actin were from Santa Cruz Biotechnology Inc. (Santa Cruz, Calif.). The blots were rinsed in TBS-T and then incubated with horseradish peroxidase-conjugated goat anti-mouse antibodies 1:10,000 for 1 h at room temperature. Antibody-antigen complexes were visualized by detecting enhanced chemiluminescence with X-ray film.

FACS Analysis

Cells were grown in 60-mm plates and treated with AICAR for 48 h. Apoptosis was evaluated using the Annexin V FITC Detection Kit (Oncogene Research Products, Cambridge Mass.). Briefly, both attached and floating cells were collected, washed with cold PBS, re-suspended at a density of $5\times10^5$/ml in 0.5 ml DMEM, stained for annexin V and analyzed by flow cytometry.

Immunohistochemistry

Mice were perfused intracardially with 4% paraformaldehyde in PBS. Their brains were removed, fixed further in the same solution. 5-mM sections, cut on the same day, were de-waxed and hydrated through graded ethanols, cooked in 25 mM citrate buffer pH 6.0 in a pressure cooker at 1150 C for 3 min (decloaking chamber, Biocare Medical), transferred into boiling deinoized water and left to cool down for 20 min. After 5 min treatment in 3% $H_2O_2$, slides were incubated with rabbit polyclonal activated caspase-3 antibody diluted 1:100 in CAS-Block (Zymed) for 3 h at room temperature, washed three times with Optimax (Biogenex), incubated for 30 min with anti rabbit Envision_(DAKO) and developed with DAB for 15 min.

Catecholamine Measurements

Catecholamines were measured as described previously (Avraham et al (1996), *Brain Res.* 732, 133-144. The assays for dopamine and NE were performed by HPLC separation and detection using HPLC-ECD. Values are presented as a concentration (ng/mg tissue).

Eight-Arm Maze

The animals were placed in an eight-arm maze, which is a scaled-down version of that developed for rats (Randt et al, (1971) *Science* 172, 489-499; Ziv et al (1994) *Neuroscience Lett,* 170, 136-140). We used water deprivation achieved by limiting water consumption overnight and a reward of 50 μl of water presented at the end of each arm. The mice were tested until they made entries into all eight arms or until they completed 24 entries, whichever came first. Hence, the lower the score, the better the performance. Maze performance was calculated each day for five consecutive days. Results were presented as area under the curve (AUC) utilizing the formula: (day 2+day 3+day 4+day 5)−4*(day 1).

Statistical Analysis

Data are presented as means and standard deviations (SD) or standard errors (SEM). Results were evaluated by one-way ANOVA and 2-tailed t-test. Post-hoc testing was carried out using the Tukey-Kramer multiple comparisons procedure.

Example 1

Nutritional Depletion Induces Dose-Dependent Hippocampal AMPK Activation

To study how nutrition may modulate cognitive function, hippocampal AMPK activity in response to DR was measured. Mice were assigned at random (10 mice per group) to different levels of DR for 5 days and then sacrificed. DR to 60% led to approximately a 4-fold elevation of AMPK-phosphorylation, while for 40% DR it was 6-fold, demonstrating a dose-dependent activation of AMPK in the hippocampus in response to nutrient depletion. (FIG. 1A).

Example 2

Low Level AMPK Activation Enhances Neurogenesis and Cognition

Figure 1B:
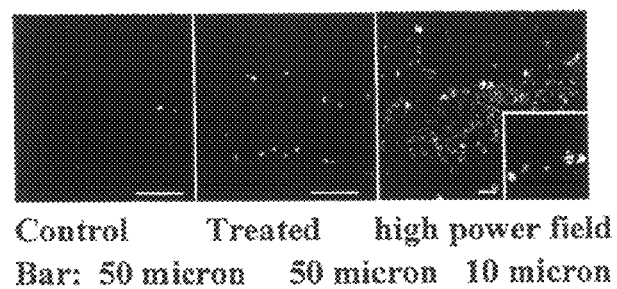
Figure 1C:
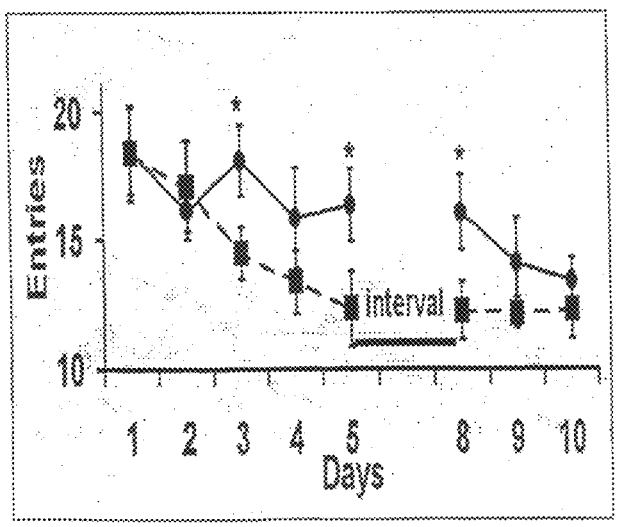

The function of AMPK activation in the hippocampus was evaluated. Since the results showed that nutrient depletion can activate AMPK over a wide range, AICAR (5-aminoimidazole-4-carboxamide ribonucleoside), a specific pharmacological activator of this kinase, was used in order to mimic these nutritional effects. Mice were treated with bromodeoxyuridine (BrdU) and either saline or 25 nM AICAR (low level stimulation) once daily for 10 days. The number of BrdU-immunoreactive cells in the dentate gyrus measures the generation rate of new cells and was significantly increased following the treatment (FIG. 1B). Next, behavioral testing was performed using the eight-arm maze to determine whether there was a concomitant improvement in cognition. Mice treated with 25 nM AICAR performed significantly better than the controls indicating that this compound has a beneficial effect on cognitive function. (FIG. 1C).

Example 3

Figure 1D:
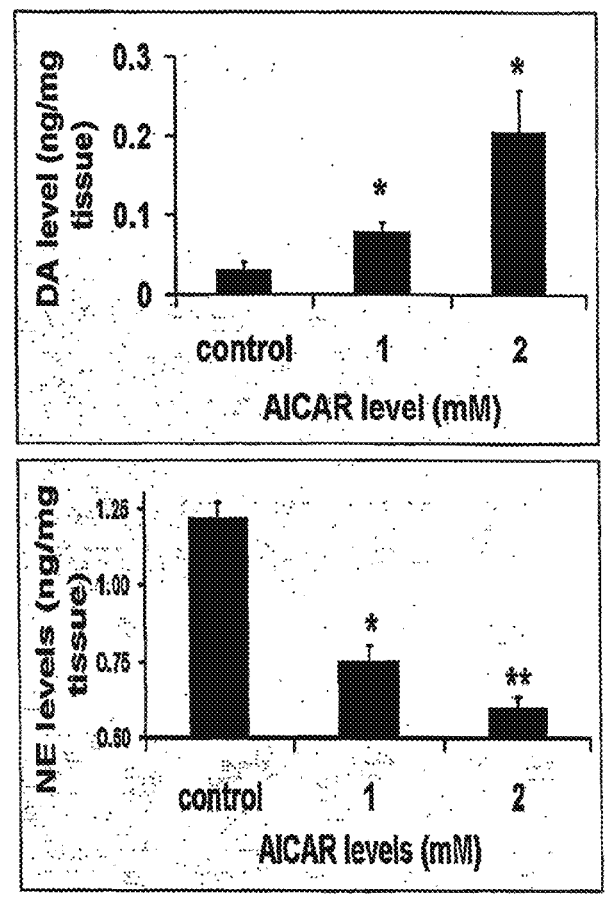
Figure 1E:
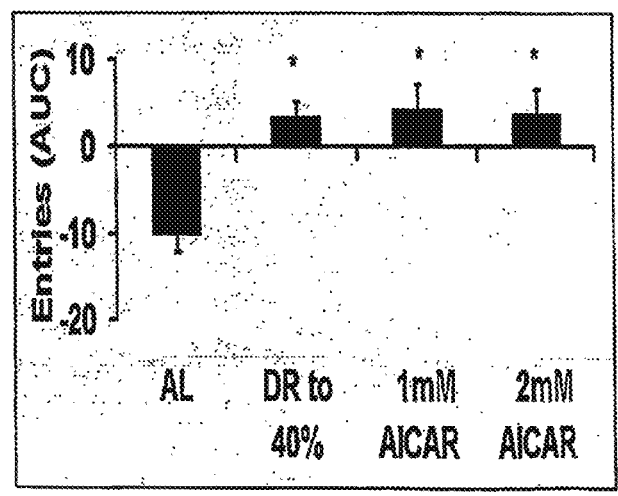
Figure 1F:
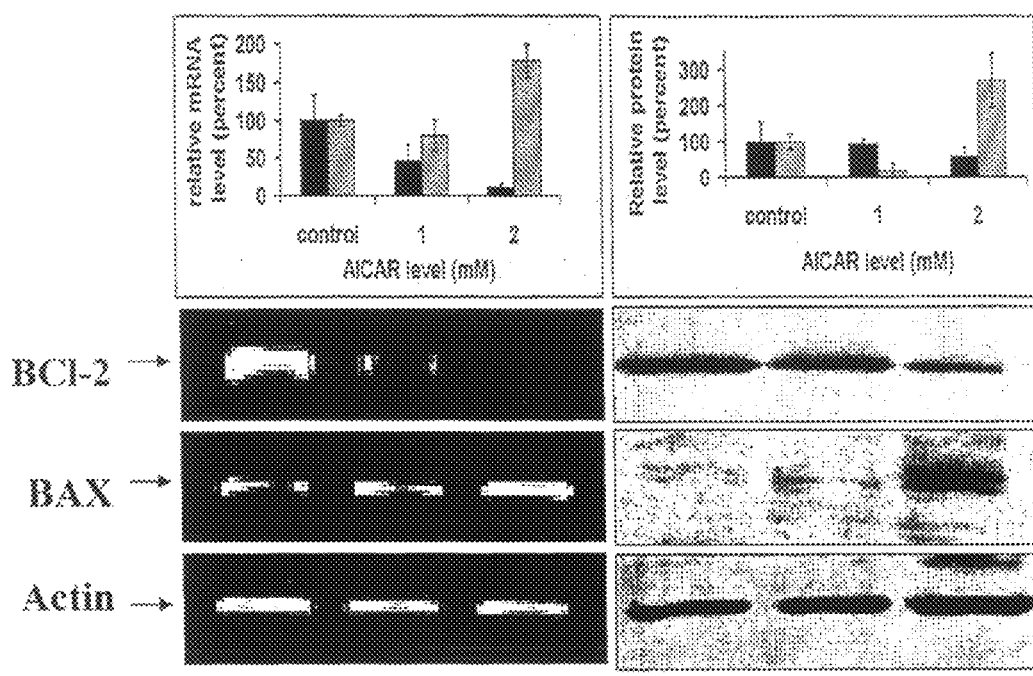

High Activation Modulates Catecholamines, Impaired Cognition and Neuro-Apoptosis To study the effect of further augmentation of hippocampal AMPK activation, mice were injected daily with higher doses of AICAR (1-2 mM) for 10 days. Such treatment decreased norepinephrine (NE) concentrations progressively ($p<0.05$, 0.01 for the two dosages, respectively) while elevating those of dopamine ($p<0.05$) (FIG. 1D). It was further asked whether these findings were associated with alterations in hippocampal-dependent spatial memory. Mice given high dose AICAR exhibited a significant deterioration in maze performance compared to the ad libitum group, and in a similar manner to mice under DR to 40% (FIG. 1E). To elucidate the cellular mechanisms involved in these AMPK effects, the proteins associated with apoptosis were measured, by RT-PCR and immunoblotting. AICAR treatment induced up-regulation of Bax while reducing bcl-2, thereby promoting apoptosis (FIG. 1F).

Example 4

High AMPK Activation Induces an Intense Apoptotic Cell Death In-Vitro

Figure 2A:
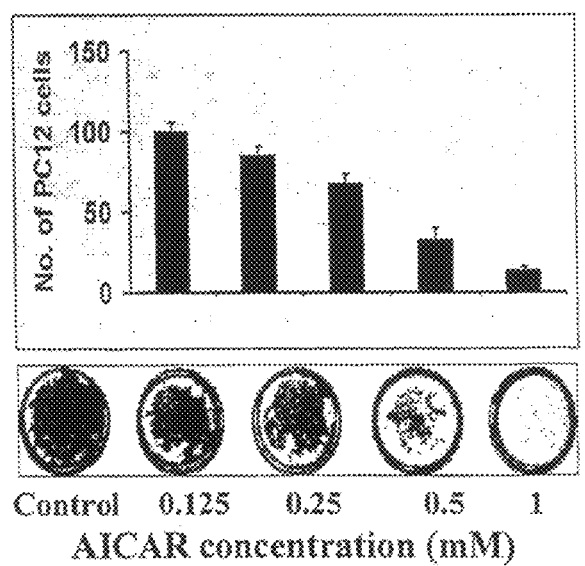
FIG. 2. Nutritional depletion induces dose-dependent AMPK activation in PC-12 cells. (A) Differentiated PC-12 cells were treated with AICAR as above and stained after 96 h. (B) The cells were co-stained with annexin V antibodies and propidium iodide, and were then analyzed by flow-cytometry. Apoptotic cells are represented by the two-right hand rectangles in each panel.

To confirm the cellular effects of AMPK in the hippocampus, in-vitro studies on PC-12 cells were also preformed. Treatment of differentiated cells with the same doses of AICAR (from 0.125 to 1.0 mM) induced a dose-dependent reduction in the number of viable cells, reaching almost total after 96 h (FIG. 2A).

The apoptotic ratio at 48 h, was also evaluated, by FACS analysis. Annexin V staining revealed that AICAR treatment induces apoptotic cell death in a dose-dependent manner (FIG. 2B).

Example 5

Nutritional Status Differentially Modulates Leptin and its Receptor Expression

Leptin is a key hormone in the regulation of energy balance and is known to modulate AMPK activity in other systems[15,16]. The manner by which leptin may interact with AMPK in modulating brain function was further investigated. Leptin was analyzed functionality under different degrees of diet restriction. Mice were assigned at random to 3 groups, and fed (AL), DR to 60% or to 40% for 10 days. Serum leptin concentrations (ELISA) decreased promptly after implementation of both DR regimens, and were nearly undetectable after 4 days (FIG. 3A). Analysis of leptin receptor expression by RT-PCR demonstrated an increasing elevation of the short form with the degree of diet restriction. Yet, while DR to 60% induced significant up-regulation of the long (functional) form of the OB receptor, this was not observed in response to 40% DR (FIG. 3B). Following these results, the effects of leptin administration on hippocampal AMPK phosphorylation was studied. Treatment of 40% diet restricted mice for 72 h with 1 mg/kg leptin significantly reduced the AMPK phosphorylation (FIG. 3C).

Example 6

Figure 4B:
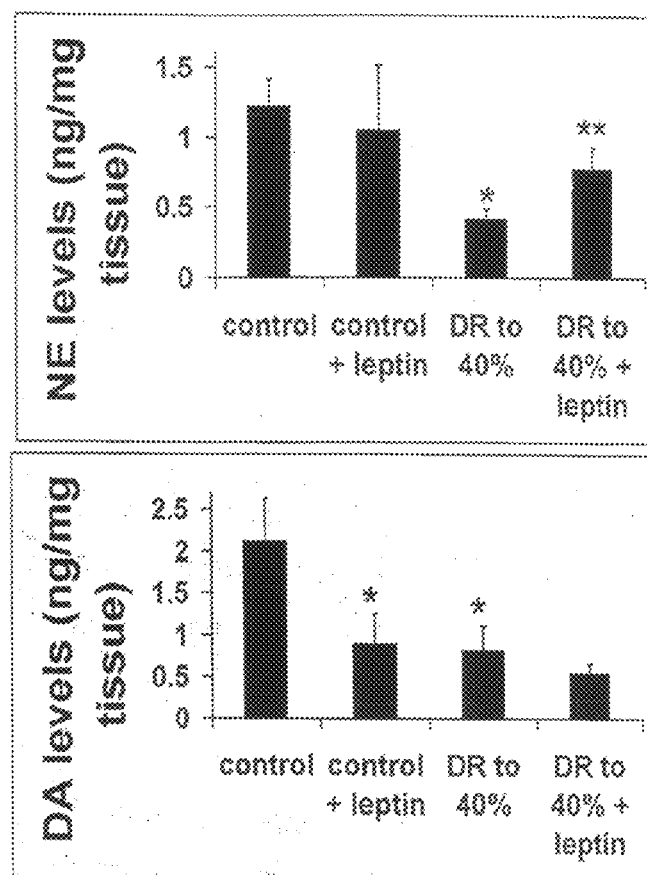
FIG. 4. Administration of leptin restored the cellular, neurochemical and behavioral effects of 40% DR. (A). Mice were treated with or without daily injections of 1 mg/kg leptin under AL or DR to 40%. Eight-arm maze was performed. (B) The effect leptin administration on catecholamine concentrations under DR to 40%. (C) Bcl-2 and Bax level was analyzed by RT-PCR and immunoblotting. Black columns represent Bcl-2 protein and the hatched columns Bax. PARP cleavage was analyzed by immunoblotting. (D) Activated caspase-3 in hippocampal sections was analyzed by immunohistochemistry.
Figure 4D:
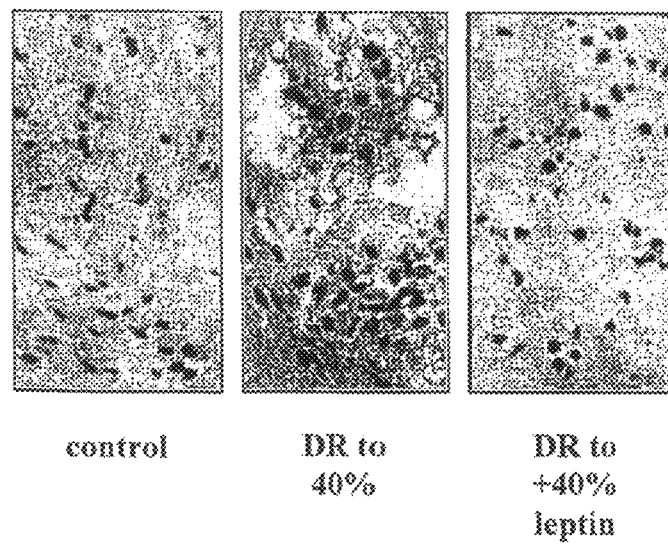
Figure 4C:
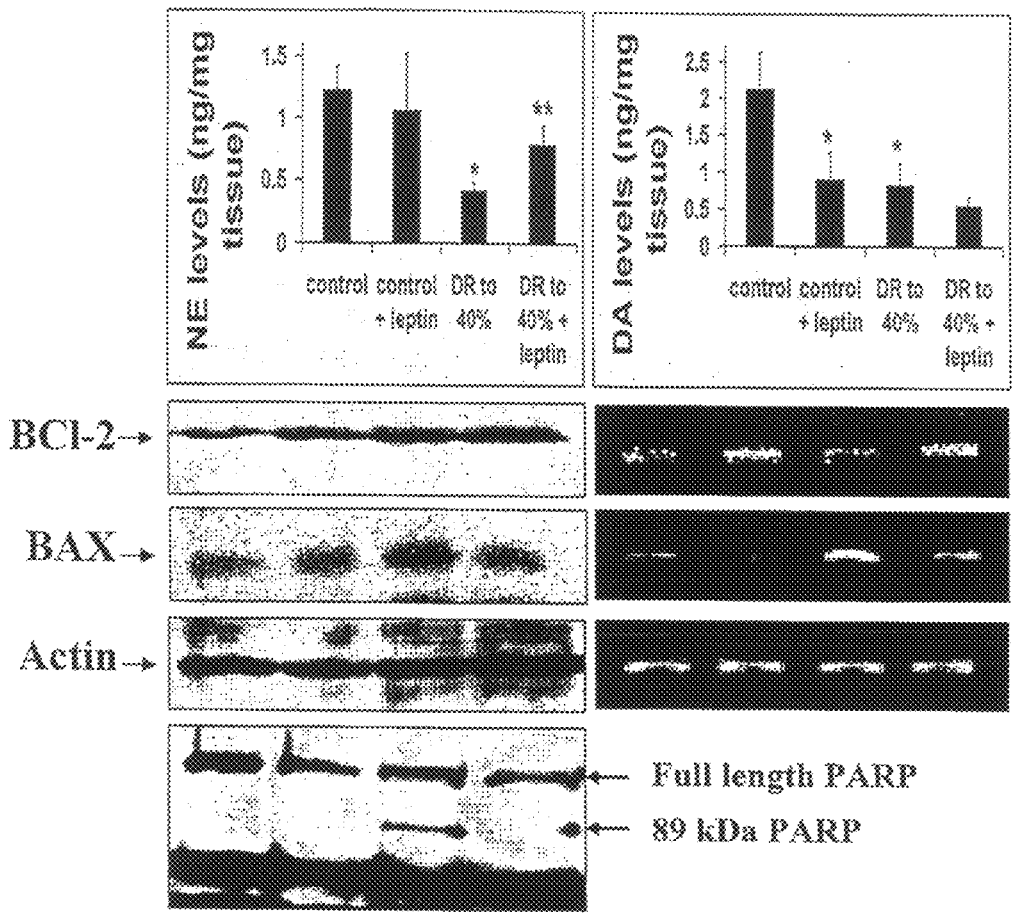

Leptin Reversed the Effects of Severe DR on Cognition Catecholamines and Neuro-Apoptosis The effects of leptin administration (restoration) on neural function in diet-restricted mice was investigated. Mice were assigned at random to 4 groups. The groups were kept under ad libitum or DR to 40% for 10 days and injected daily with either 1 mg/kg leptin or saline for 5 days during the second week. Treatment with leptin reversed the impaired eight-arm maze performance associated with DR to 40%; the control group was not affected by leptin administration (FIG. 4A). Cognitive performance improvement was also observed in the Morris Water Maze (data not shown). Then the effects on the concentrations of NE and dopamine in the hippocampus were evaluated. Treatment with leptin reversed the reduction of NE following DR. Leptin down-regulated dopamine concentrations in the AL group yet did not induce any significant reduction in the DR group in which dopamine concentrations were already reduced (FIG. 4B). To elucidate the cellular mechanisms involved in leptin effects, proteins associated with apoptosis were determined by immunoblotting. Leptin induced up-regulation of bcl-2 while reducing Bax levels. Analysis of PARP cleavage demonstrated a reduction in the cleaved subunit following leptin treatment, suggesting an increase in the direction of survival (FIG. 4C). The anti-apoptotic effect of leptin was further confirmed by detection of activated caspase-3 expression as ?of apoptotic cell death. Activated caspase-3 could not be detected in the hippocampi of control animals. Leptin significantly reduced the immunoreactivity of the activated caspase-3 found following 40% DR (FIG. 4D).

Example 7

Leptin Increases Survival Under Severe Energy Restriction

Figure 5A:
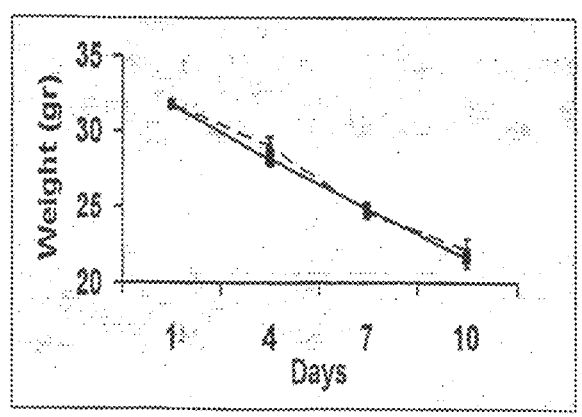
FIG. 5. Leptin increases survival under severe energy restriction. Evaluation of body weight and survival of 40% DR mice during treatment with either saline or 0.05 mg/kg/h leptin, continuously injected from a subcutaneous 200 µl mini-osmotic pump. Number and weight of living mice were documented every day for 16 days.
Figure 5B:
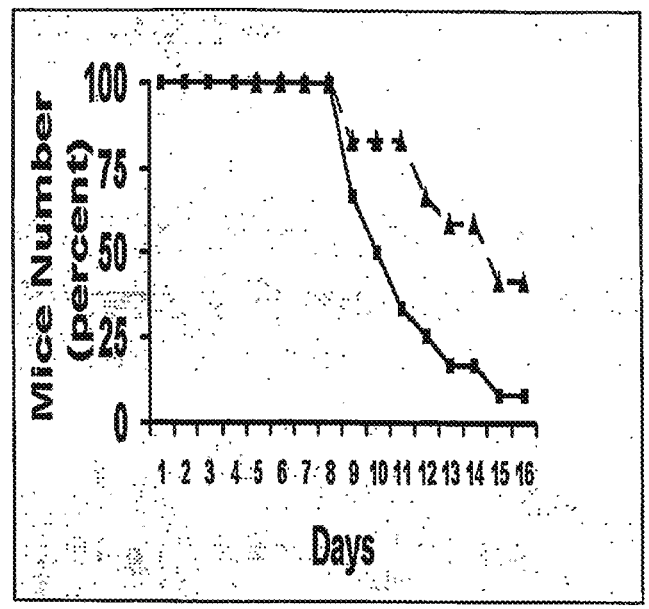

Severe energy restriction leads to deterioration of neural function and eventually death. Since leptin can improve cognitive function following DR to 40% and prevents neural apoptosis, it was investigated whether it may also promote mice survival under these same severe conditions. In the first experiment, mice were fed ad libitum or DR to 40% for 12 days and injected daily with 1 mg/kg leptin or saline during the second week (5 days). 95% of the mice survived with leptin treatment compared to 65% in the control group ($p<0.05$). In a second experiment, mini-osmotic pumps delivering 0.05 mg/kg/h leptin or saline continuously for 16 days were implanted in mice under 40% DR (12 animals in each group). Despite a similar weight loss, leptin-treated mice survived significantly longer (Kaplan Meir log rank, $p<0.05$, 1-tail). The 50% survival in the treated group increased from 9 to 14 days. (FIG. 5).

Example 8

Leptin Prevents Cell Death Caused by Glucose Depravation

Figure 7:
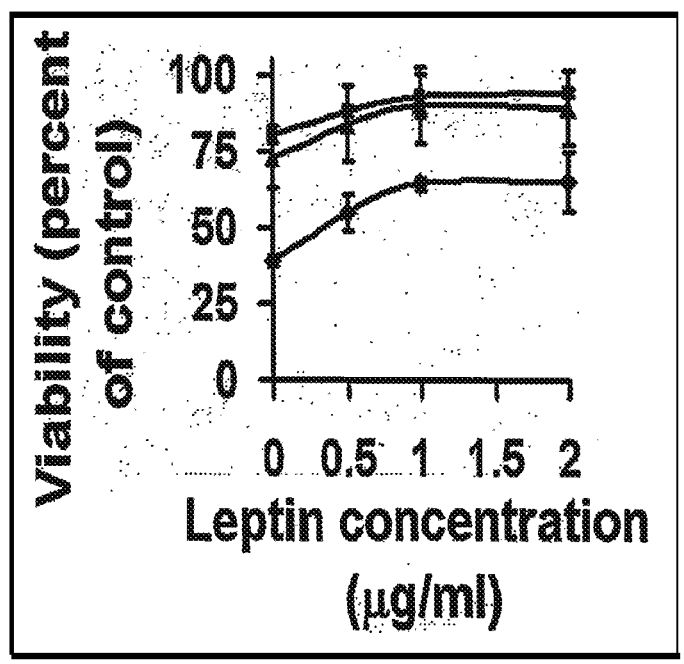
FIG. 7 Leptin induces survival after nutritional stress. Cultured cardiomyocytes exposed to glucose deprivation for 1, 3, 6 h were treated with Leptin. Cell viability was analyzed by WST.

Cultured cardiomyocytes were exposed to glucose deprivation for 1, 3, 6 h and were treated with Leptin as described above. Cell viability was analyzed by WST. Results are shown in FIG. 7. Leptin increased significantly the viability of the cardiomyocytes after glucose deprivation.

Cultured cardiomyocytes exposed to glucose deprivation for 1, 3, 6 h were treated with Leptin. Stat-3 phosphorylation (A) and AKT phosphorylation (measure for cell survival and cardioroprotection) were measured by protein analysis. The results are shown in FIG. 8 can be seen leptin administration improved the cell survival as measured by AKT phosphorylation.

Leptin decreased apoptosis following conditional stress. Cultured cardiomyocytes exposed to glucose deprived condition for 1, 2, 6 h were treated with 1 ug/ml Leptin. Apoptotic cell death was detected by FACS analysis In another experiment cultured cardiomyocytes exposed to glucose deprived condition for 1, 2, 6 h were treated with 1 ug/ml Leptin. Apoptotic cell death was detected by FACS analysis. The results are shown in FIG. 9. As can be seen leptin reduced apoptotic death caused by glucose deprivation.

Example 9

Figure 10:
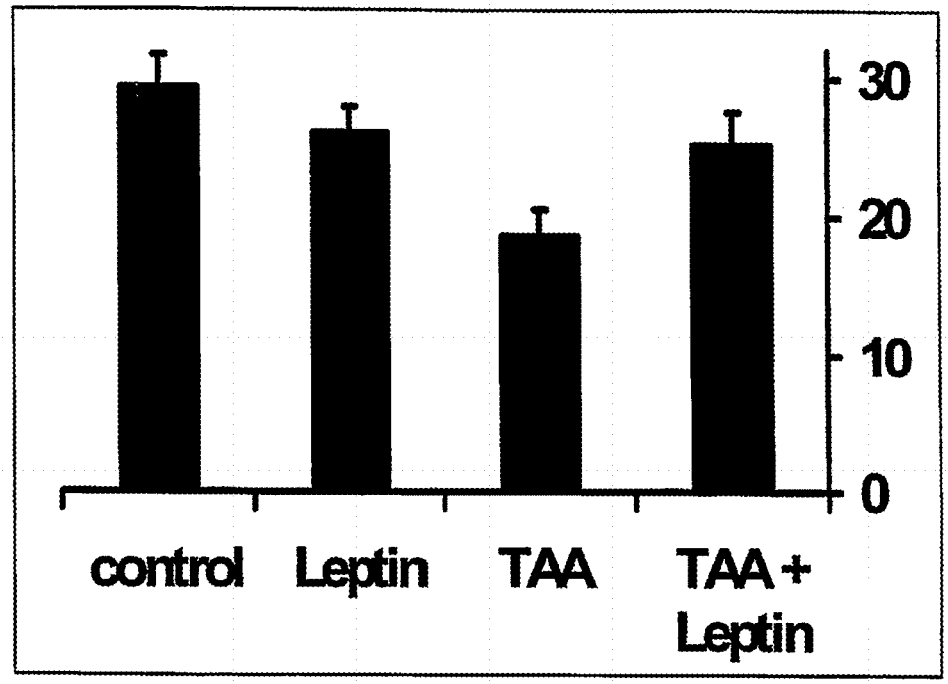
Figure 11:
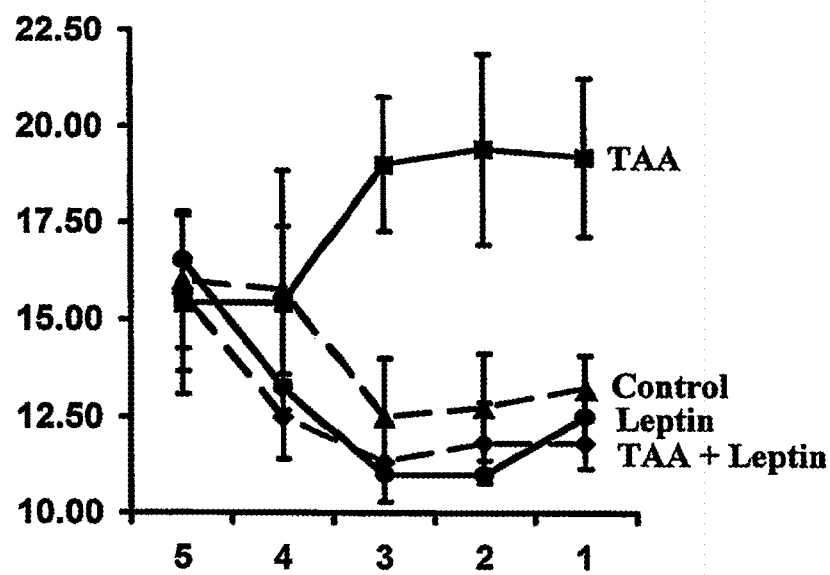
FIG. 11. Leptin reversed impaired cognitive function in experimental model of Hepatic encephalopathy. Mice were treated with TAA, then 1 mg/kg Leptin was administered daily for 5 days. Cognitive function was evaluated in the eight arm maze.

Leptin Improved Neurological Score, Activity and Cognitive Function and Prolongs Survival in an Experimental Model of Hepatic Encephalopathy Mice were treated with TAA to cause an experimental hepatic encephalopathy-brain damaged caused by liver dysfunction and common in people whose liver function deteriorates. The activity index of the animals was assessed. As can be seen in FIG. 10, Leptin was able to reverse activity in diseased animals to the level of health controls—indicating the potential of leptin in preventing deterioration of cognitive function caused by hepatic encephalopathy. FIG. 11. Leptin reversed impaired cognitive function in experimental model of Hepatic encephalopathy.

Figure 12:
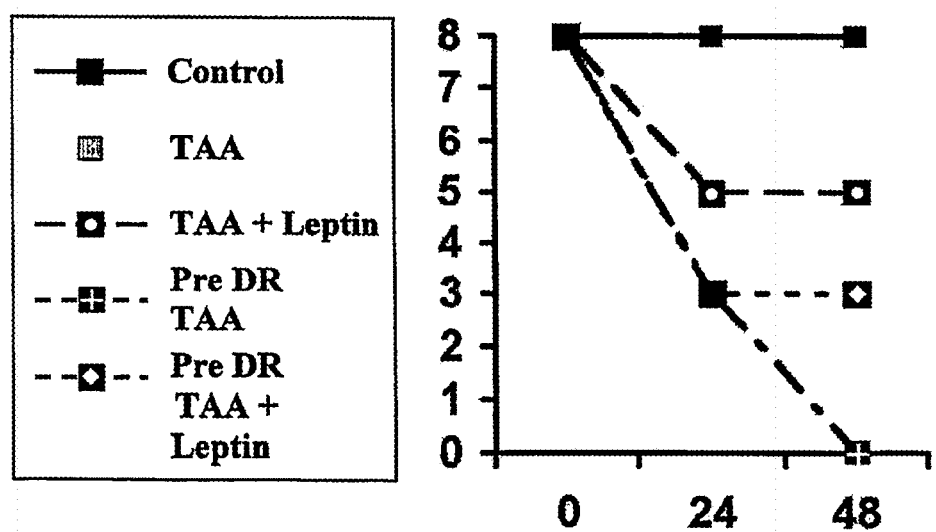
FIG. 12. leptin decreases mortality in an experimental model of hepatic encephalopathy. Mice were maintained on Ad Librium or DR to 40% conditions. TAA was administered with or without leptin. Treated mortalilty rate was recorded everyday.
Figure 13:
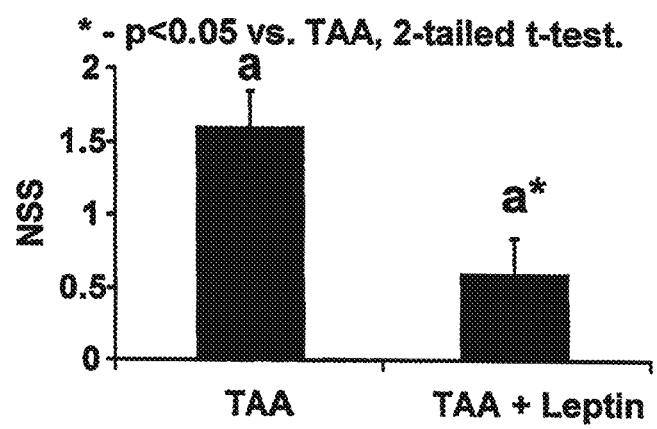
FIG. 13 Leptin reversed impaired neurological score in an experimental model of hepatic encephalopathy. Mice were treated with TAA, then 1 mk/kg Leptin was administered daily for 5 days and neurological score was evaluated FIG. 14 Leptin improved impaired cognitive function caused by LPS. LPS administered mice were daily treated with 1 mg/kg leptin and then subjected to the eight arm maze. As can be seen, Leptin was able to reverse cognitive function in diseased animals to the level of health controls—indicating the potential of leptin in preventing deterioration of cognitive function caused by hepatic encephalopathy.

FIG. 12. Leptin decreased mortality in an experimental model of hepatic encephalopathy. FIG. 13 Leptin reversed impaired neurological score in an experimental model of hepatic encephalopathy.

Example 10

Leptin Improved Impaired Cognitive Function Caused by LPS

Figure 14:
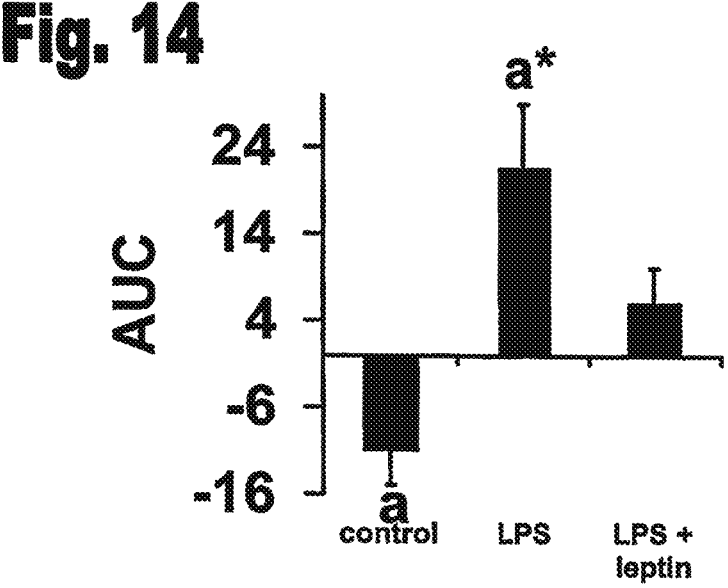

LPS administered mice were daily treated with 1 mg/kg leptin and then subjected to the eight arm maze. As can be seen in FIG. 14, Leptin was able to reverse cognitive function in diseased animals to the level of health controls—indicating the potential of leptin in preventing deterioration of cognitive function caused by hepatic encephalopathy.

REFERENCES

1. During, M. J., Cao, L., Zuzga, D. S., Francis, J. S., Fitzsimons, H. L., Jiao, X., Bland, R. J., Klugmann, M., Banks, W. A., Drucker D. J. and Haile, C. N. (2003) *Nat. Med.* 9, 1173-1179.
2. Maruyama, W., Weinstock, M., Youdim, M. B., Nagai, M. and Naoi, M. (2003) *Neurosci. Lett.* 341, 233-236.
3. Cameron, H. A. and McKay, R. D. (2001) *J. Comp. Neurol.* 435, 406-417.
4. Lee, J., Seroogy, K. B. and Mattson, M. P. (2002) *J. Neurochem.* 80, 539-547.
5. Turner, E. (1969) *Lancet* 2, 1123-1126.
6. Shors, T. J., Miesegaes, G., Beylin, A., Zhao, M., Rydel, T. and Gould, E. (2001) *Nature* 410, 372-376.
7. Hardie, D. G. and Carling, D. (1997) *Eur. J. Biochem.* 246, 259-273. Review.
8. Campas, C., Lopez, J. M., Santidrian, A. F., Barragan, M., Bellosillo, B., Colomer, D. and Gil, J. (2003) *Blood* 101, 3674-3680.
9. Meisse, D., Van de Casteele, M., Beauloye, C., Hainault, I., Kefas, B. A., Rider, M. H., Foufelle, F. and Hue, L. (2002) *FEBS Lett.* 526, 38-42.
10. Ido, Y., Carling, D. and Ruderman, N. (2002) *Diabetes* 51, 159-167.
11. Andersson, U., Filipsson, K., Abbott, C. R., Woods, A., Smith, K., Bloom, S. R., Carling, D. and Small, C. J. (2004) *J. Biol. Chem.* 279, 12005-12008.

12. Minokoshi, Y., Alquier, T., Furukawa, N., Kim, Y. B., Lee, A., Xue, B., Mu, J., Foufelle, F., Ferre, P. and Bimbaum, M. J. (2004) *Nature* 428, 569-574.
13. Lee, G. H., Proenca, R., Montez, J. M., Carroll, K. M., Darvishzadeh, J. G., Lee, J. I. and Friedman, J. M. (1996) *Nature* 379, 632-635.
14. Chua, S. C. Jr., Chung, W. K., Wu-Peng, X. S., Zhang, Y., Liu, S. M., Tartaglia, L. and Leibel, R. L. (1996) *Science* 271, 994-996.
15. Montague, C. T., Farooqi, I. S., Whitehead, J. P., Soos, M A., Rau, H., Wareham, N. J., Sewter, C. P., Digby, J. E., Mohammed, S. N., Hurst, J. A., Cheetham, C. H., Earley, A. R., Barnett, A. H., Prins, J. B. and O'Rahilly, S. (1997) *Nature* 387, 903-908.
16. Minokoshi, Y., Kim, Y. B., Peroni, O. D., Fryer, L. G., Muller, C., Carling, D. and Kahn, B. B. (2002) *Nature* 415, 339-343.

The invention claimed is:

1. A method for treating undesirable manifestations of a nutritional stress condition selected from the group consisting of sepsis, prolonged post-surgical stress, prolonged post injury stress, brain damage caused by liver disease; and weight loss associated with severe malnutrition, a mal-absorption condition that can lead to chronic malnutrition, malnutrition caused by cancer or infection, or anorexia, comprising:
 administering to a subject having said nutritional stress condition a therapeutically effective amount of one or more agents selected from the group consisting of:
  a leptin protein, a fragment of a leptin protein having physiological properties of the leptin protein, variant leptin protein or variant of a fragment of a leptin protein fragment having physiological properties of the leptin protein,
  a leptin receptor agonist being a leptin mimic, and
  an activator of the AMPK signal transduction pathway,
 wherein the subject is other than one having Alzheimer's Disease.

2. The method according to claim 1, wherein the agent is a leptin protein.

3. The method according to claim 1, wherein the agent is a leptin mimic selected from the group consisting of:CBT1452 and {D-LEU-4}-OB3.

4. The method according to claim 1, wherein the agent is an activator of the AMPK transduction pathway selected from the group consisting of: TSC2; LKB1; AICAR and metformin.

5. The method according to claim 4, wherein the activator of the AMPK transduction pathway is in an amount that causes low level activation of the pathway.

6. The method according to claim 1, wherein the nutritional stress condition is selected from the group consisting of weight loss associated with celiac disease, colitis, carbohydrate intolerance, or HIV infection.

7. The method according to claim 1, wherein the undesirable manifestation of nutritional stress condition is a decrease in cognitive function.

8. A method for improving cognitive function in a subject having diminished cognitive function due to a condition selected from the group consisting of stroke, hepatic encephalopathy, Parkinson, Huntington Chorea and other neurodegenerative processes associated with cachexia, comprising:
  administering to a subject having diminished cognitive function due to a condition selected from the group consisting of stroke, hepatic encephalopathy, Parkinson, Huntington Chorea and other neurodegenerative processes associated with cachexia, a therapeutically effective amount, in a daily dose of 0.02-10 mg/kg, of one or more agents selected from the group consisting of:
    a leptin protein, a fragment of a leptin protein having physiological properties of the leptin protein, variant leptin protein or variant of a fragment of a leptin protein fragment having physiological properties of the leptin protein,
    a leptin receptor agonist being a leptin mimic, and
    an activator of the AMPK signal transduction pathway,
  wherein the subject is other than one having Alzheimer's Disease.

* * * * *